Figure 1:
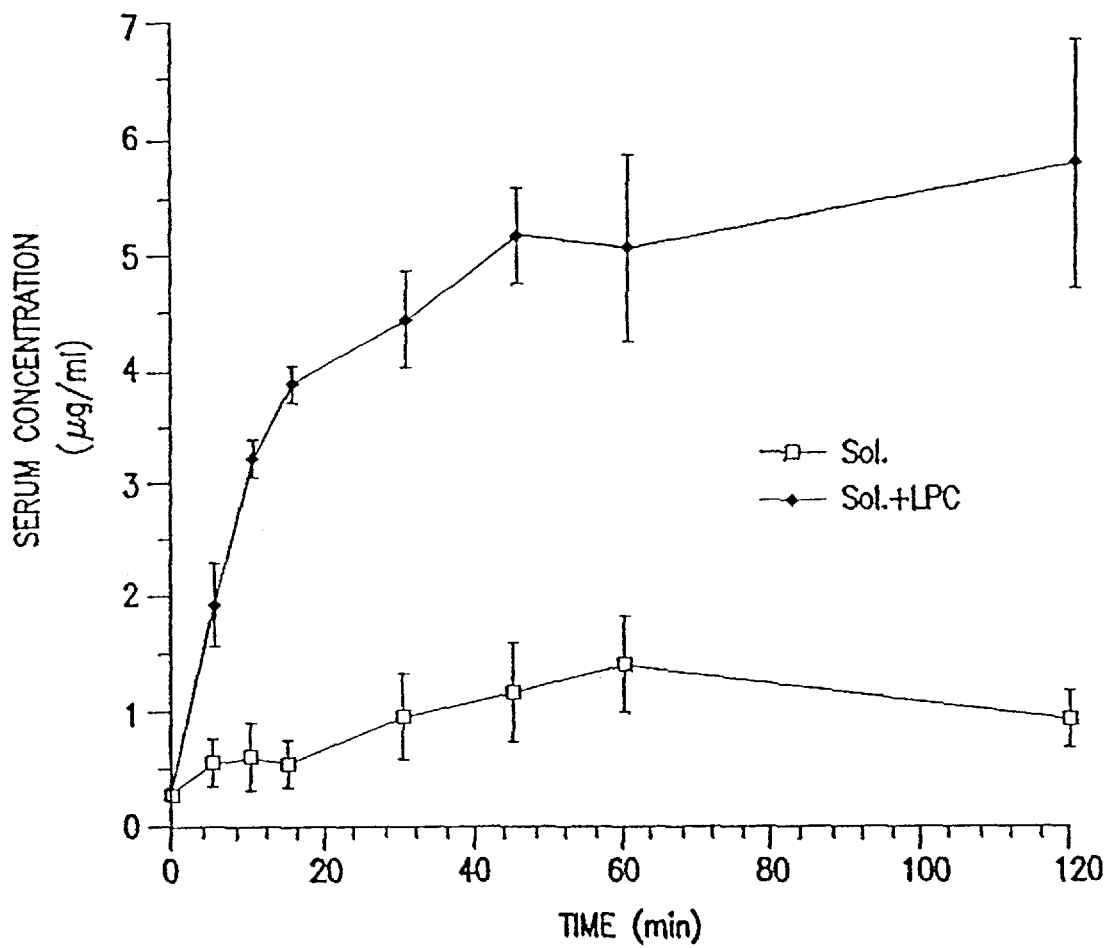

US005863554A

United States Patent [19]

Illum

[11] Patent Number: 5,863,554
[45] Date of Patent: Jan. 26, 1999

[54] ENHANCED UPTAKE DRUG DELIVERY SYSTEM

[75] Inventor: Lisbeth Illum, The Park, United Kingdom

[73] Assignee: Danbiosyst UK Limited, Nottingham, United Kingdom

[21] Appl. No.: 899,976

[22] Filed: Jul. 24, 1997

Related U.S. Application Data

[62] Division of Ser. No. 412,094, Mar. 28, 1995, Pat. No. 5,690,954, which is a continuation of Ser. No. 142,844, Oct. 25, 1993, abandoned, which is a continuation of Ser. No. 865,855, Apr. 9, 1992, abandoned, which is a continuation-in-part of Ser. No. 760,854, Sep. 17, 1991, abandoned, which is a continuation of Ser. No. 424,320, Nov. 20, 1989, abandoned.

[30] Foreign Application Priority Data

Jan. 31, 1995 [WO] WIPO ............... PCT/EP95/00622

May 22, 1997 [GB] United Kingdom ............... 8712176

[51] Int. Cl.$^6$ ............................................. A61K 9/16
[52] U.S. Cl. ................... 424/434; 424/489; 424/499; 424/500; 424/501; 424/502
[58] Field of Search ................... 426/434, 489–502

[56] References Cited

U.S. PATENT DOCUMENTS 5,690,954  11/1997  Illum ................................ 424/434

*Primary Examiner*—Gollamudi S. Kishore
*Attorney, Agent, or Firm*—Arnall Golden & Gregory, LLP

[57] ABSTRACT

A drug delivery system including a plurality of microsphere particles containing an active drug and including a material associated with each particle which material has the property of increasing the bioavailability of the active drug.

9 Claims, 17 Drawing Sheets

ENHANCED UPTAKE DRUG DELIVERY SYSTEM

This is a divisional of U.S. Ser. No. 08/412,094 filed Mar. 28, 1995, now U.S. Pat. No. 5,690,954, which is a continuation of U.S. Ser. No. 08/142,844 filed Oct. 25, 1993, now abandoned, which is a continuation of U.S. Ser. No. 07/865,855 filed Apr. 9, 1992, now abandoned, which is a continuation-in-part of U.S. Ser. No. 07/760,854 filed Sep. 17, 1991, now abandoned, which is a continuation of U.S. Ser. No. 07/424,320 filed Nov. 20, 1989, now abandoned. U.S. Ser. No. 07/424,320 claims priority under 35 U.S.C. §119 to PCT GB88/00396 filed May 20, 1988.

FIELD OF THE INVENTION

The present invention relates to drug delivery systems and more particularly to a system which enhances the uptake of active drug material, particularly high molecular weight materials, especially from the nasal cavity.

References will be made to technical papers and other disclosures within this field which are included for purposes of explanation.

European patent applications 023,359 and 122,023 describe a powdery pharmaceutical composition for application to the nasal mucosa and methods for administration thereof. The pharmaceutical composition allows polypeptides and derivatives thereof to be effectively absorbed through the nasal mucosa. Similarly U.S. Pat. No. 4,250,163 describes a method for administering a medicament to the nasal mucosa where the preferred composition has mucoadhesive properties. European Patent application 123,831 has described how the use of biocompatible water soluble amphiphilic steroids other than natural bile salts are capable of increasing drug permeability across body surfaces to include the nose. The German Patent 2620446 describes an aqueous insulin preparation for nasal application containing a penetration enhancer in the form of an amphoteric, anionic or nonionic surface active agents, saponin, bile salts or surfactin. European patent application 230,264 describes an aqueous nasal drug delivery system for vaccines containing a high molecular weight drug, a gelling agent (e.g. hydroxyethylcellulose) and in some cases other additives (e.g. surfactants, glycerol, polyethyleneglycol).

None of the above patents and applications describes the use of microspheres for nasal administration nor the combination of a microsphere and an enhancing agent or other adjuvants that would be expected to provide enhanced bioavailability.

A microsphere preparation for nasal delivery has been described in PCT/GB86/00721 however this refers to materials having ion exchange properties and for one specific drug sodium chromoglycate for local effect rather than delivery to the general circulation.

At the present time the nose is being proposed as an alternative route for the delivery of drugs that will act within the systemic circulation. Particular attention is being focused on products of biotechnology, namely the peptides and proteins. Other drugs that are being suggested are those that are poorly absorbed orally or are extensively metabolised either in the gastro-intestinal tract itself or are subjected to first pass metabolism in the liver.

Nasal delivery is considered to have promise for the following reasons.

1. The nose has a large surface area available for drug absorption due to the coverage of the epithelial surface by numerous microvilli.
2. The subepithelial layer is highly vascularized.
3. The venous blood from the nose passes directly into the systemic circulation and therefore avoids the loss of drug by first pass metabolism in the liver.

A wide variety of drugs has now been tested for bioavailability after administration via the nasal route. Some drugs appear to be absorbed effectively and show bioavailabilities comparable to the intravenous route. However, most drugs show a low bioavailability when administered intranasally, but there are exceptions. The natural steroid progesterone is largely ineffective when administered orally. When given by the nasal route it is absorbed effectively with a bioavailability similar to that for an intravenous injection; the peak concentration appearing after approximately 6 minutes. If progesterone is given via the oral route then published data suggest that the bioavailability is of the order of 1.2% as compared to IV administration (1). The second example is the beta-blocker propanolol. This drug is metabolised extensively in the liver and possibly in the gut wall when administered orally. When the drug is given intranasally in a simple solution, plasma levels identical to intravenous administration can be obtained (2).

Insulin, a drug that has been studied extensively for intranasal delivery, can be delivered across the nasal membrane but the absorption efficiency is normally about 1.2% of the administered dose. Absorption can be improved by the use of so-called absorption enhancers. For example in a study by Salzman insulin was administered in the presence of a surfactant, Laureth 9 (3). Not only was a clear dose response relationship obtained but also the peak level appeared rapidly. The potency of the intranasal insulin was approximately 1/10th that of intravenous administered insulin. Clearly if insulin can be delivered to patients in a safe and reliable way by nasal administration then such systems could have potential for administration with meals in type 1 diabetes.

Chien and Chang (4) have summarised the absorptive capacity of the nasal routes for a variety of drug substances. It will be noted that those materials of high molecular weight, i.e. peptides and proteins are normally poorly absorbed via the nasal route. Also is noted the fact that most of the compounds, both those with high and low absorption efficiencies, show peak plasma levels within approximately 30 minutes. Thus absorption, whatever its extent, appears to be rapid but does not last for a particularly long time. This indicates that the drug may either be removed from the site of absorption or, if sufficiently labile, is degraded before further absorption can occur.

Factors affecting systemic absorption of drugs from the nose

The rapid clearance of nasal sprays from the nose can probably be considered to be a major factor in influencing loss of drugs from potential absorption surfaces. In addition, for the case of peptides and proteins, enzymatic degradation of the drug and molecular size may also have a role in giving low bioavailabilities.

Most workers in the field of nasal delivery have attempted to overcome the problem of inefficient absorption of drugs by using absorption enhancers e.g. in the form of bile salts or surfactants to modify the properties of the nasal mucosa thereby enhancing uptake. A typical example is the investigation described by Hanson et al (5) on the nasal delivery of the peptide salmon calcitonin. Here she showed clearly that a significant increase in plasma calcitonin could occur when the drug was given in combination with a surfactant. Thus, without enhancer only trace amounts of calcitonin appeared in the plasma whereas with enhancer involved the AUC increased 10 fold. Similarly, the striking effect of increasing amounts of bile salt (sodium deoxycholate) on the absorption of insulin has been well described by Gordon and others (6).

Controlled release systems for the nose

Illum et al (7) have chosen microspheres made from materials that are known to swell in contact with water to form a gel-like layer with good bioadhesive properties. Thus, due to their adherence to the nasal mucosa they could well modify clearance. The materials selected included albumin, starch and the ion exchange material DEAE-Sephadex. the size of the microspheres has been of the order of 40–60 µm in diameter.

The clearance of labelled microspheres from the nose has been studied in human volunteers using the standard technique of gamma scintigraphy (7). The microspheres were labelled with technetium-99m and applied to the nose in powder form using a nasal insufflator. Liquid and powder formulations were used as controls. The position of the noses of the volunteers was held constant on the collimator of the gamma camera using a specially designed template. Scintiscans were obtained over a suitable time period and regions of interest were created around the site of deposition in the nasal cavity. The time-activity profiles showed clearly that the nasal spray and powder formulations are cleared quite rapidly (with a time for 50% clearance ($T_{50\%}$) of 15 minutes). In contrast, the microsphere systems have a much longer clearance time. After 3 hours about 50% of the albumin and starch micro-spheres and 60% of the DEAE-Sephadex microspheres still remain at the site of application. The half-time of clearance from this initial deposition site for DEAE-Sephadex microspheres were calculated to be about 4 hours. At the present time we are exploring whether these microsphere systems will provide an enhancement of the bioavailability of selected drug substances to include peptides and proteins. We expect that a decreased clearance rate and the possible protection of labile drugs against enzymatic attack will significantly increase absorption efficiency.

In relation to controlled release systems and the nose it is interesting to note that Nagai and colleagues (8) have been able to increase the absorption of insulin after nasal application to dogs by using a gelling formulation. Insulin was mixed with a cellulosic material and Carbopol 934 (polyacrylic acid) and applied as a powder formulation. Similarly, Morimoto and colleagues (9) have used a nasal gel (once again polyacrylic acid) as a delivery system for insulin and calcitonin in rats. A significant decrease in plasma glucose levels obtained as compared to the normal formulation indicated an increase in the absorption efficiency.

A major problem in drug delivery is the effective absorption of high molecular weight materials such as proteins and peptides across biological membranes. Normally such molecules are not taken up by the body if administered to the gastrointestinal tract, to the buccal mucosa, to the rectal mucosa, the vaginal mucosa or given as an intranasal system.

As discussed above and by Chien and Chang (4) recent studies with insulin have demonstrated that the absorption of such a compound can be increased if it is given together with a so-called absorption enhancer. These absorption enhancing materials have included surfactants of the non-ionic type as well as various bile salt derivatives. An increased permeability of membranes in the presence of these types of surfactant materials is not unexpected, indeed the literature in the field of gastroenterology contains a wide range of such absorption promoters. (For a review see Davis et al (10).

However, such materials may not be acceptable for the chronic administration of pharmacological agents because of their irritant effects on membranes. This includes not only the non-ionic variety of surface active agents but also bile salts and bile salt derivatives (e.g. fusidic acid).

It is an object of the present invention to provide a drug delivery system which enhances delivery of high molecular weight materials.

The present invention therefore provides a drug delivery system including an absorption-enhancing amount of non-liquid microsphere particles containing a non-toxic physiologically effective amount of active drug and including a material associated with each particle, which material has the property of increasing the bioavailability of the active drug across a mucosal membrane.

Preferably the particles are administered in the form of a powder by spraying and have bioadhesive properties.

The preferred materials for increasing the bioavailability of the drug are phospholipids and lysophosphatidyl compounds such as lysolecithin, lysophosphatidyl-ethanolamine, lysophosphatidylglycerol, lysophosphatidyl-serine, lysophosphatidic acid etc. Other phospholipid compounds soluble in water can be expected to demonstrate similar effects for example short chain phosphatidylglycerol and phosphatidylcholine. A suitable concentration is from 0.02 to 10%.

This material should not produce any problems in terms of chronic toxicity because in vivo the material should be non-irritant and/or rapidly metabolised to a normal cell constituent that does not have any significant irritant effect.

Embodiments of the present invention will now be described by way of example with reference to the accompanying drawings, in which:

FIG. 1 illustrates in graphical form the effect of the use of the bioavailability improving material on the uptake of a drug in a first experiment;

FIG. 2 illustrates in graphical form the effect of the use of the bioavailability improving material and the administration in the form of microspheres;

FIG. 3 illustrates in graphical form the effect of the use of the material in a rat study experiment;

FIGS. 4 and 5 respectively show plasma glucose levels for rabbits given intranasal doses of Zn and Na insulin;

FIG. 6 shows plasma glucose levels obtained for administration intranasally of insulin in different forms;

FIG. 7 shows corresponding curves for plasma insulin levels;

FIG. 8 shows data from rat experiments with hGH given intranasally;

FIG. 9 shows data from sheep experiments with hGH given intranasally;

FIG. 10 shows mean % plasma glucose following administration of insulin with glycodeoxycholate alone and with starch microspheres;

FIG. 11 shows the corresponding plasma levels for FIG. 10;

FIG. 12 shows the effect of administration of insulin together with acyl-carnitine and starch microspheres on plasma glucose;

FIG. 13 shows the effect of administration of insulin with lysophosphatidylcholine-myristoyl alone and with starch microspheres;

FIG. 14 shows the effect of administration of insulin with lysophosphatidylglycerol alone and with starch microspheres;

FIG. 15 shows the effect of administration of insulin with chitosan alone and with starch microspheres;

Figure 16:
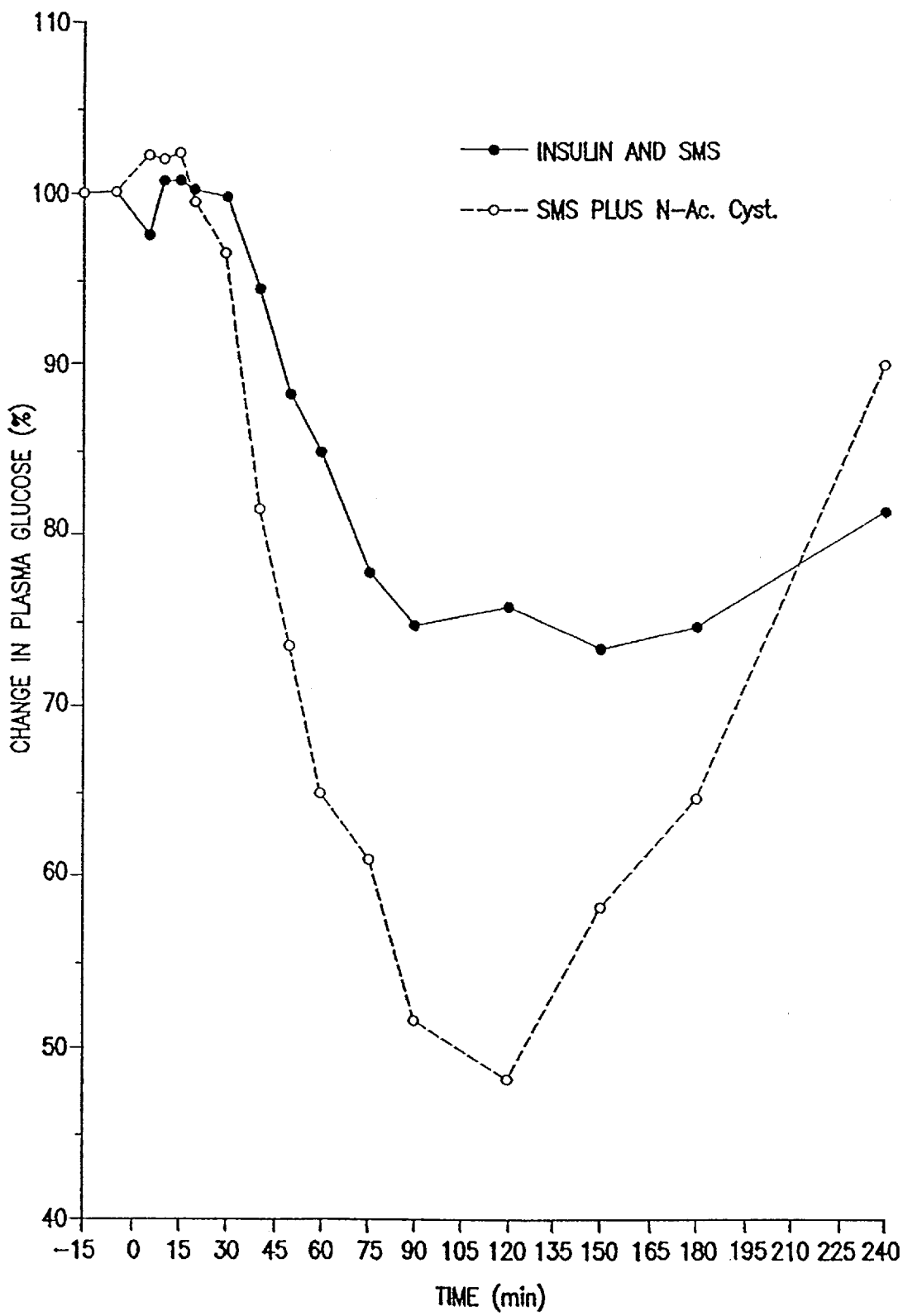
Figure 17:
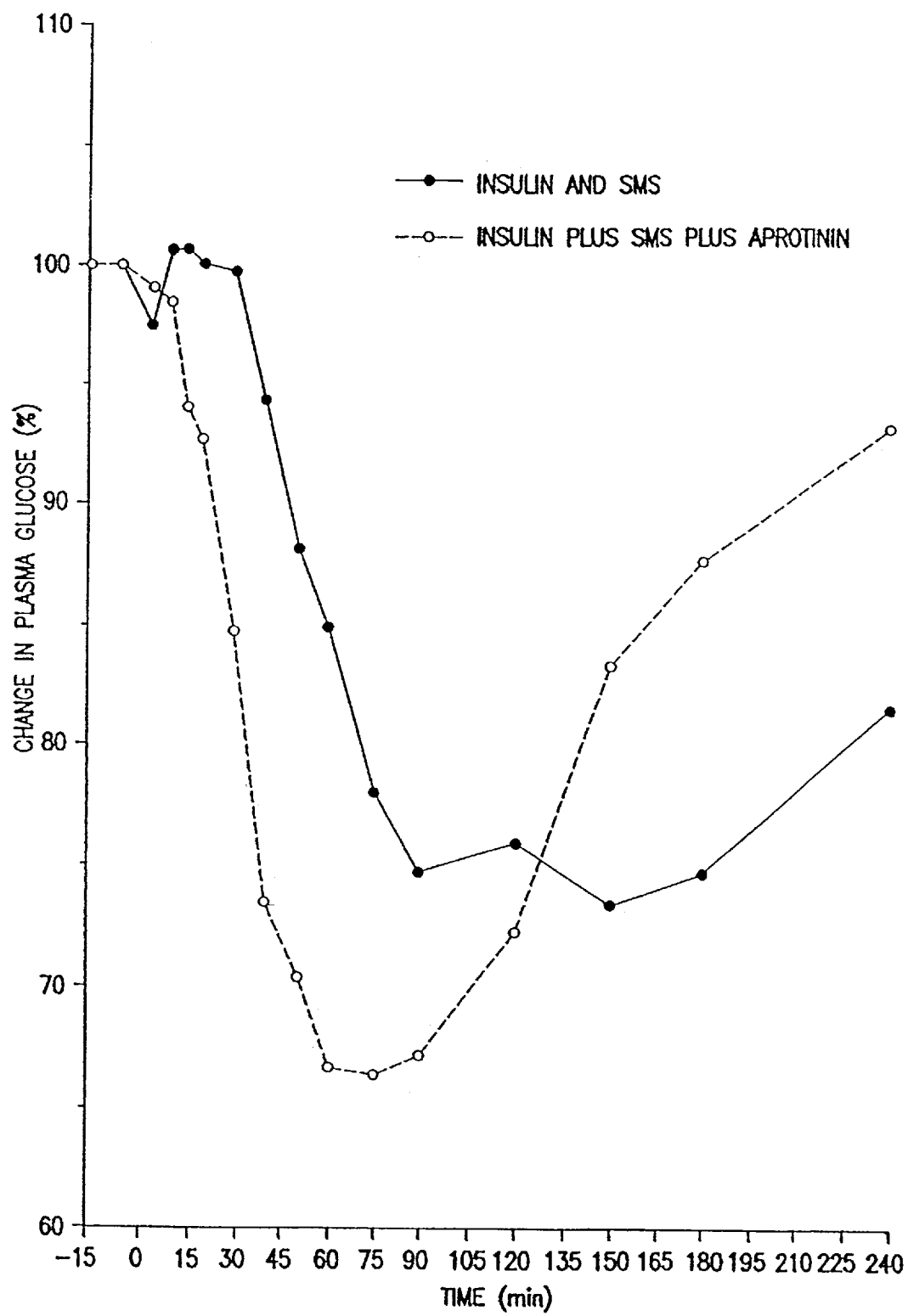

FIG. 16 shows the comparison of administration of insulin with starch microspheres alone and together with N-acetyl cysteine; and FIG. 17 shows a similar comparison to FIG. 16 using aprotinin.

The drug to be administered to a mucosal surface in the gastrointestinal tract, the eye, genital tract or the nose or lung could be administered as a viscous solution, a suspension or a powder, together with a bioavailability improving material or more preferably it should be administered in the form of a colloidal particle comprising a microsphere system. The advantage of using bioadhesive microsphere systems for administration to the mucosal surface is that such systems should allow a longer period of contact, especially if the microspheres are slowly degrading. This is particularly true for the nasal administration of drugs contained in microspheres produced from natural materials such as albumin, gelatin and especially starch.

In the present invention phospholipids and lysophosphatides such as lysoleuthin are the preferred material to be added to the active drug to act as to increase the bioavailability of the drug. Lysophosphatides are produced by the hydrolysis of phospholipids. Such materials are surface active and form micellar structures.

Lysophosphatidylcholine changes the permeability of membranes and allows the increased uptake of proteins and peptides including; for example, insulin, human growth hormone and other products of biotechnology and recombinant DNA methodologies. After administration the lysophosphatides are converted by the cells of the endothelial lining of the mucosa to the intact phosphatides which are normal cell components (see de Vries et al (11). (Lysolecithin itself is also present in cell membranes in very small quantities (12)). This rapid and efficient conversion of lysophosphatides into the complete phosphatide structure leads to much reduced adverse reactions and side effects in terms of irritation and toxicity.

A preferred material is the material lysophosphatidylcholine produced from egg or soy lecithin. Other lysophosphatidylcholines that have different acyl groups as well as lyso compounds produced from phosphatidylethanolamines, phosphatidylglycerols and phosphatidic acid which have similar membrane modifying properties may be used. Water soluble phospholipids with short acyl chains will also be appropriate since these are surface active. Acyl carnitines (e.g. Palmitoyl-DL Carnitine-chloride) are an alternative.

Other enhancing agents that are appropriate for use in the present invention include phosphatidylglycerols, lysophosphatidylglycerols, lysolecithins, chelating agents (EGTA, EDTA, alginates), surface active agents (especially non-ionic materials), acyl glycerols, fatty acids and salts, tyloxapol, chitosan, cyclodextrins, glycyrrhetinates and biological detergents listed in the SIGMA Catalog, 1988, page 316–321. Also agents that modify the membrane fluidity and permeability would be appropriate such as Enamines (e.g. phenylalanine enamine of ethyllacetoacetate), Malonates (e.g. diethyleneoxymethylene malonate), Salicylates, Bile salts and analogues and fusidates. Suitable concentrations would be up to 10%.

The same concept of delivery of a drug incorporated into or onto a bioadhesive microsphere with an added pharmaceutical adjuvant would apply to systems that contained active drug and mucolytic agent, peptidase inhibitors or irrelevant polypeptide substrate singly or in combination. A suitably mucolytic would be thiol-containing compounds such as N-acetylcysteine and derivatives thereof. Peptide inhibitors include actinonin, amastatin, antipain, bestatin, chloroacetyl-HO-Leu-Ala-Gly-$NH_2$, diprotinin A and B, ebelactone A and B, E-64, leupeptin, pepstatin A, phosphoramidon, H-Thr-(tBu)-Phe-Pro-OH, aprotinin, kallikrein, chymostatin, benzamidine, chymotrypsin, trypsin. Suitable concentrations would be from 0.01 to 5%.

The microspheres should be of a size between 10 and 100 microns and prepared from a biocompatible material that will gel in contact with the mucosal surface. Starch microspheres (cross linked if necessary) are a preferred material. Other microspheres include gelatin, casein, dextrans, alginate, ararose, albumin, collagen, chitosan, poly vinylacetate, hyuluronic acid esters and polylae-. Preparation of these microsphere systems is well described in the pharmaceutical literature (see for example Davis et al (13)). Emulsion and phase separation methods are both suitable. The final microspheres can be modified by chemical crosslinking using agents such as 2,3-butadione, 1,5-glutaraldehyde and sodium trimetaphosphate or heat treatment. For example, microspheres according to the invention were prepared as follows:

Preparation of starch microspheres

Starch microspheres were prepared by an emulsion technique as follows:

5 g potato starch were dissolved in 95 ml of water at about 90° C. A second solution was prepared from 3 g of polyethylene glycol ($M_w$=6000) and 47 ml of water. This solution was heated to about 70° C., whereafter the warm starch solution was added while stirring, to form an emulsion. When the two-phase system had formed (with the starch solution as the inner phase) the mixture was allowed to cool to room temperature under continued stirring, wherewith the inner phase was converted to gel particles. The particles were filtered off at room temperature and slurried in 100 ml of ethanol, whereafter the particles were again filtered off and laid to dry in air.

The yield was 90%.

Soluble potato starch microspheres was prepared by a coacervation technique as follows:

15 ml 5% starch solution (pH=7) was kept at a constant temperature of 70° C. and stirred (500 rpm) while a 30% solution of polyethylene glycol was added (~7 ml) until phase separation had occurred, the system was stirred for further 15 min before it was cooled on ice during constant stirring. The microspheres were then isolated by filtration and freeze-dried. With a stirring speed of 500 rpm particles with a mean size of 33 $\mu m \pm \mu m$ was produced.

Preparation of Albumin microspheres

Albumin microspheres were produced by an emulsification technique. 50 ml of highly purified olive oil was mixed with 75 ml of petroleum ether and prestirred for 5–10 min in a 125 ml beaker using a Heidolph mixer. To this mixture 0.4 ml of 25% w/v aqueous solution of rabbit serum albumin (RSA) in phosphate buffer (pH 7.4) was added dropwise and stirring was continued at 700 rpm for 15 min. The microspheres were stabilised by adding dropwise 0.1 ml of a 25% w/v glutaraldehyde solution under continual stirring for 15 min. The microspheres were isolated by centrifugation, washed with petroleum ether, filtered through a Millipore filter, washed again with petroleum ether and then ethanol and freeze-dried overnight.

The size of the microspheres was in the range of 40–60 $\mu$m.

Since the size of the microspheres was found to increase when drug was incorporated the manufacturing procedure was adjusted using a stirring speed of 900 rpm in order to obtain microspheres of the desired size range.

Albumin microspheres were prepared by a coacervation technique as follows:

10 ml 25% HSA solution (pH=5) was stirred (500 rpm) while a 30% solution of PEG was added (~2,5 ml) until phase separation occurred. The system was stirred for 15 min before the albumin droplets was solidified by slowly heating the mixture to 90° C. and keeping it at this temperature for 30 min. Instead of heat denaturation, glutaraldehyde can be used to crosslink the albumin but this latter method seems to make the particles aggregate to a greater extent than that seen with the heat denaturation. The microspheres were then isolated by filtration and freeze-dried.

With a stirring speed of 500 rpm particles with a mean size of 43 µm±6 µm was produced.

Preparation of Gelatin microspheres

Gelatin microspheres were prepared by an emulsion technique as follows:

100 ml olive oil (70° C.) was mixed with 10 ml 5–10% gelatin solution and the mixture was stirred at 500–1500 rpm keeping the temperature constant at 70° C., the emulsion is stirred for 15 min and was then cooled on ice during constant stirring. The microspheres were isolated by filtration, washed and freeze-dried.

A concentration of 10% gelatin and a stirring speed of 1000 rpm gives a mean particle size of 70 µm±µm.

Gelatin microspheres were prepared by a coacervation technique as follows:

30 ml 10% bovine gelatin (pH=8.5) was kept at a constant temperature of 50° C. and stirred (500 rpm) while a 30% solution of PEG was added (~20 ml) until the coacervation region was reached. To control this step a nephelometer can be used. The mixture was cooled on ice during constant stirring. The microspheres were isolated by filtration and freeze-dried.

With a stirring speed of 500 rpm particles with a mean size of 60 µm±10 µm was produced.

Preparation of Chitosan microspheres

Chitosan microspheres were prepared by an emulsion technique as follows:

Chitosan, as for example a glutamate salt (70% degree of deacetylation) was dissolved in water to a concentration of 5% w/v. 100 ml Soybean oil was mixed with 10 ml of the 5% Chitosan solution to form a water in oil emulsion. The microspheres were stabilized by adding dropwise 0.1 ml of a 25% w/v glutaraldehyde solution under continual stirring for 15 minutes. The microspheres were isolated by centrifugation, washed and freeze-dried. The size of the microspheres was in the range 10–90 µm.

The active agent can be incorporated into the microspheres during their formulation or sorbed into/onto the system after preparation. For example, rose bengal and sodium cromoglycate were used as model drugs for demonstration of incorporation into the microspheres.

Albumin microspheres were prepared as described above by an emulsion technique with a stirring speed of 900 rpm and the model drug dissolved in the albumin solution at various concentrations.

Concentrations of 0.5, 2, 4 and 5% w/v Rose bengal were used. Above 5% w/v the aqueous phase became too viscous and microspheres did not form. Due to the solution characteristics of sodium cromoglycate in water the highest concentration that could be used was 8% w/v. Thus, microspheres were manufactured from solutions containing 0.5, 1, 2 and 4% w/v sodium cromoglycate.

The maximum loading capacities for these compounds were found to be 170 µg Rose bengal and 137 µg sodium cromoglycate per mg albumin microspheres.

200 mg of starch microspheres (freeze-dried) were added to 4 ml of sodium cromoglycate solution (80 mg/ml) and left for about half an hour to swell. The microspheres were separated from the solution by centrifugation and washed with water to remove excess of drug and then freeze-dried.

The preparation of the starch-insulin system was carried out by adding the freeze dried starch microspheres to a phosphate buffer solution (pH=7.3) containing the insulin and the enhancer system, mixing for 1 hour and freeze drying until a light powder was obtained. A typical concentration of insulin and enhancer system (e.g. lysolecithin) would be 1 IU/mg/microsphere and 0.08 mg/mg microspheres, respectively. The micro-spheres can be loaded with both less or more drug and enhancer system. For example, starch microspheres in combination with insulin and lysophosphatidylcholine were made by preparing a solution of 107.13 mg insulin in 30 ml of water (3.571 mg/ml, 100 IU/ml. A 10 ml solution of the enhancer, lysophosphatidylcholine was prepared at 10 mg/ml in water. 10 ml of insulin solution were mixed with the enhancer solution and the required quantity of microspheres (1 g) were dispersed in the solution and the resultant suspension stirred for one hour at room temperature, and then freeze-dried to obtain the power formulation.

The freeze-drying were performed on an Edwards Modulyo freeze-dryer fitted with a bell-jar assembly and operated at a pressure of 0.08 torr, a condenser temperature of −53° C. and a product shelf temperature of 20° C. The freeze-drying process were allowed to proceed for 24 hours after which the final product were loaded into the administration devices and then stored with dessicant at 4° C. for 16 hours prior to administration.

The effectiveness of the system can be controlled by the physical nature of the microsphere matrix and e.g. the extent of the crosslinking. The microsphere delivery systems could also include micro-spheres made from the active peptide or protein itself such as insulin microspheres.

Using the combination of microspheres and bioavailability increasing material, it has been found that the bioadhesive microsphere systems have the ability to greatly enhance the bioavailability of polar drugs when they are administered together with the system. This improvement is very much greater than the enhancement that can be achieved by the material itself. This potentiation of action is believed to be due to the greater retention of the delivery system in the nasal cavity. The concept has been shown to be successful for different drugs such as gentamicin, insulin, calcitonin, CCK, DDVAP and growth hormone. The material selected for these studies has been lysophosphatidylcholine (described above). The concept should work equally well with other materials (see list elsewhere) and with other drugs such as:

Insulin (hexameric/dimeric/monomeric forms)

Glucagon

Growth Hormone (Somatotropin)

Polypeptides or their derivatives (preferably with a molecular weight from 1000 to 300,000)

Calcitonins and synthetic modifications thereof

Enkephalins

Interferons (especially Alpha-2 Interferon for treatment of common colds)

LHRH and analogues (Nafarelin, Buserelin, Zolidex)

GHRH (Growth hormone releasing hormone)

Secretin

Nifedipin

Bradykin antagonists

GRF (Growth releasing factor)

THF
TRH (Thyrotropin releasing hormone)
ACTH analogues
IGF (Insulin like growth factors)
CGRP (Calcitonin gene related peptide)
Atrial Natriuretic Peptide
Vasopressin and analogues (DDAVP, Lypressin)
Antibiotics
Metoclopramide
Migraine treatment (Dihydroergotamine, Ergometrine, Ergotamine, Pizotizin)
Nasal Vaccines (Particularly AIDS vaccines)
FACTOR VIII
G-CSF (granulocyte-colony stimulating factor)
EPO (Erythropoitin)

Antibiotics and antimicrobial agents such as tetracycline hydrochloride, leucomycin, penicillin, penicillin derivatives and erythromycin, chemotherapeutic agents such as sulphathiazole and nitrofurazone; local anaesthetics such as benzocaine; vasoconstrictors such as phenylephrine hydrochloride, tetrahydrozoline hydrochloride, naphazoline nitrate, oxymetazoline hydrochloride and tramazoline hydrochloride; cardiotonics such as digitalis and digoxin; vasodilators such as nitroglycerin and papaverine hydrochloride; antiseptics such as chlorhexidine hydrochloride, hexylresorcinol, dequalinium chloride and ethacridine; enzymes such as lysozyme chloride, dextranase; bone metabolism controlling agents such as vitamin $D_3$ and active vitamin $D_3$; sex hormones; hypotensives; sedatives; and anti-tumor agents.

Steroidal anti-inflammatory agents such as hydrocortisone, prednisone, fluticasone, predonisolone, triamcinolone, triamcinolone acetonide, dexamethasone, betamethasone, beclomethasone, and beclomethasone dipropionate; non-steroidal anti-inflammatory agents such as acetaminophen, aspirin, aminopyrine, phenylbutazone, mefenamic acid, ibuprofen, diclofenac sodium, indomethacin, colchicine, and probenecid; enzymatic anti-inflammatory agents such as chymotrypsin and bromelin seratiopeptidase; anti-histaminic agents such as diphenhydramine hydrochloride, chlorpheniramine maleate and clemastine; anti-allergic agents (antitussive-expectorant antasthmatic agents such as sodium cromoglycate, codeine phosphate, and isoprotereol hydro-chloride.

Administration

The microspheres can be administered via the nasal route using a nasal insufflator device. Example of these are already employed for commercial powder systems intended for nasal application (e.g. Fisons Lomudal System). Details of other devices can be found in the pharmaceutical literature (see for example Bell, A. Intranasal Delivery devices, in Drug Delivery Devices Fundamentals and Applications, Tyle P. (ed), Dekker, New York, 1988).

The microspheres can be administered to the vagina in a freeze dried powder formulation. The microspheres are administered in a vaginal applicator and once in the vagina, the microspheres are released by pressing a syringe-type piston or similar release mechanism on the applicator. Once released, the microspheres will take up water and form a gel.

The microspheres can be administered to the eye in a gel formulation. Before administration, the microspheres could conveniently be contained in a two compartment unit dose container, one compartment containing the freeze-dried microsphere preparation and the other compartment containing normal saline. Prior to application, the two compartments are mixed and a gel is formed, which is then administered to the eye.

Animal nasal delivery studies

The following studies of nasal delivery in animal models (rats, rabbits and sheep) has been carried out in order to substantiate the invention.

Gentamicin:

The drug gentamicin was chosen as a model test substance. This polar compound is known to be poorly absorbed when administered into the nose (see for example Duchateau et al (17) and the biological availability can be enhanced by added bile salts.

Rat Studies:

The in situ rat model of Hirai et al (14) was used as modified by Fisher et al (15). Male Wistar rats of about 200 g were anaesthetized by intraperitoneal injection of 60 mg/kg of Pentobarbitone (Sagatal, 60 mg/ml). The rats were tracheotomized, the oesophagus sealed and the carotid artery cannulated.

A volume of the gentamicin solution containing 0.5% of the drug with and without added lysophosphatidylcholine (LPC) (0.2%) was instilled into the nasal cavity. Blood samples were withdrawn from the carotid artery at 0, 5, 10, 15, 30, 45, 60 and 120 min after drug administration. The gentamicin level was determined by the EMIT method (16). The effect of the LPC enhancer is demonstrated in FIG. 1. The administration of gentamicin solution alone resulted in a poor bioavailability whereas the adding of the enhancer system gave rise to a five fold greater peak level. The AUC's (from t=0 to t=120 min) were 128 and 557 $\mu$g min/ml, respectively.

Sheep studies:

Cross-bred (Suffolk and Texel) sheep were divided into groups of 3 and 2. The mean weight of the sheep was about 40 kg.

The animals were not fasted prior to the administration of gentamicin. An in-dwelling Viggo secalon universal central venous catheter of 1.2 mm, i.d. with a secalon universal flow-switch was placed in the right jugular vein of each animal on the first day of the study and whenever necessary was kept patent by flushing with heparinised normal saline (50 IU/ml). The catheter was removed upon completion of the study. For intranasal administration, the sheep were sedated by an IV dose of Ketamine hydrochloride at 2 mg/kg to prevent sneezing during administration. The sedation lasted about 3 minutes. The animals that received gentamicin by the IV route were also sedated.

For the intranasal administration of solutions, a blueline umbilical cannula of 35 cm length (size 6 FG) was inserted into the nostril of the sheep to a preset depth of 10 cm before the delivery of the solution from a 1 ml syringe. For intranasal administration of powdered formulations, a BOC endotracheal tube (red rubber, cuffed) of 6.5 mm was loaded with the powder formulation and then inserted into the nostril of the sheep to a preset depth of 6 cm before blowing the powder into the nasal cavity.

The first group of sheep (n=2) was given 0.25 ml of gentamicin solution (386 mg/ml) (5.0 mg/kg) into each nostril. The second group (n=3) received 0.25 ml of gentamicin solution (386 mg/ml) (5.0 mg/kg) containing 2 mg/ml LPC into each nostril. The third group (n=3) received 5.0 mg/kg gentamicin and 0.2 mg/kg LPC in combination with starch microspheres (1.9 mg gentamicin-/mg starch microspheres). The last group of sheep (n=3) was given 2 mg/kg gentamicin administered intravenously as a solution (40 mg/ml) through the jugular vein. Blood samples (2 ml) were collected through the jugular vein at 0, 8, 16, 24, 32, 45, 60, 90, 120, 180 and 240 min after drug administration. The serum was separated by centrifugation and the samples stored at −20° C. awaiting analysis. No heparin was added to any of the samples. The gentamicin level was determined by the EMIT technique (16).

Figure 2:
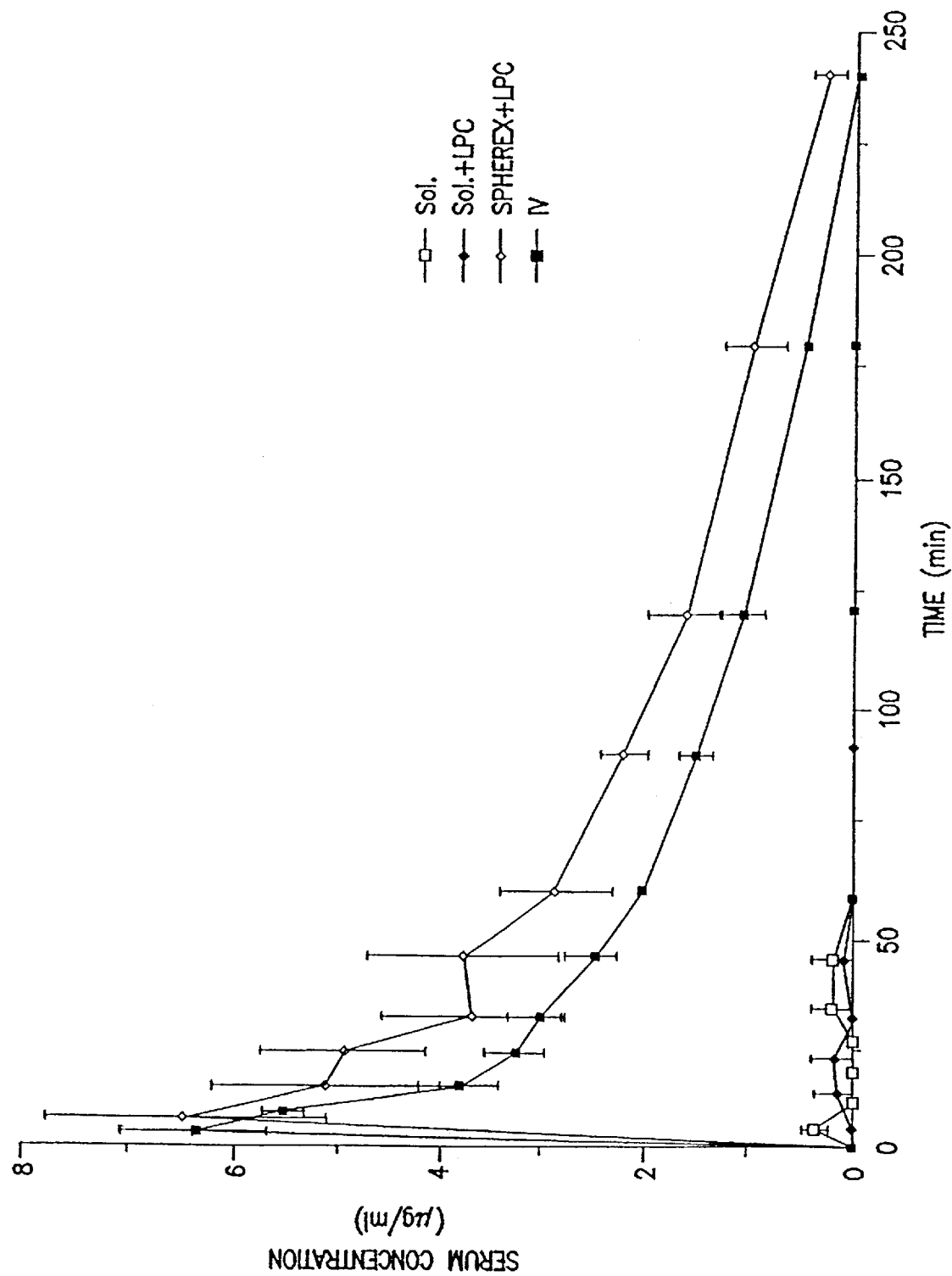

A dramatic effect is seen when the gentamicin plus enhancer are administered in the form of the starch microsphere formulation, the blood level peaking at 6.3 μg/ml as compared to 0.4 μg/ml for gentamicin solution. The combination of microspheres plus LPC enhancer provides a blood level-time profile that is very similar to that obtained when gentamicin is given intravenously (FIG. 2).

The fact that a sharp peak is obtained using a combination of drug with microspheres and bioavailability increasing material is very surprising. The studies of Illum et al (7) would suggest that to show clearance of bioadhesive microspheres from the nasal cavity would result in the absorption of drug from the nasal cavity at longer time periods. That is the plasma level—versus the profile should be flat for a controlled release perforation. This is not found; the increase in absorption occurs at the earlier time periods. It is therefore suggested that besides acting in a bioadhesive capacity the microspheres are affecting the tight junctions of the cells in the nasal mucosa thereby allowing greater drug uptake. This effect on tight junction integrity appears to occur during the gelling process, perhaps as a result of removal of water from the cells in the mucosa to the microspheres.

Accounting for the doses administered the bioavailability for the intranasally administered gentamicin in combination with the LPC and gelling microsphere system is 57.3% as compared to the gentamicin given by IV dose.

Insulin

In all animal studies the glucose plasma levels were analysed using the glucose oxidase method. The plasma insulin levels were determined for the rabbit and sheep experiments by means of radioimmune assay using a double-antibody technique.

Rat Studies:

The Hirai's in situ model (as modified by Fisher) was used to study the nasal absorption of insulin using non-diabetic male Wistar Rats of 150 g fasted overnight. The rats were anaesthetized with an i.p. injection of 0.25 ml of Pentobarbitone (60 mg/ml).

A 250 IV/ml solution of Zinc (Zn)-human insulin was prepared in buffer (1/75M $Na_2HPO_4$)) of pH 7.3. In some experiments 0.2% of LPC or for comparison it Glycodeoxycholate (GDC) were added to the preparation as absorption enhancers. The experiments were performed in replicate (n=4). 10 μl was administered into the nasal cavity equivalent to 16.67 IV/kg (2.5 IV/rat). Blood samples (0.2 ml) were collected into 5 ml fluoride oxalate tubes at 10, 6 and 2 min pre-administration and at 5, 10, 20, 40, 60, 90, 120, 180, 240 and 300 min post-administration. The blood was replaced by saline administered through the jugular vein.

Figure 3:
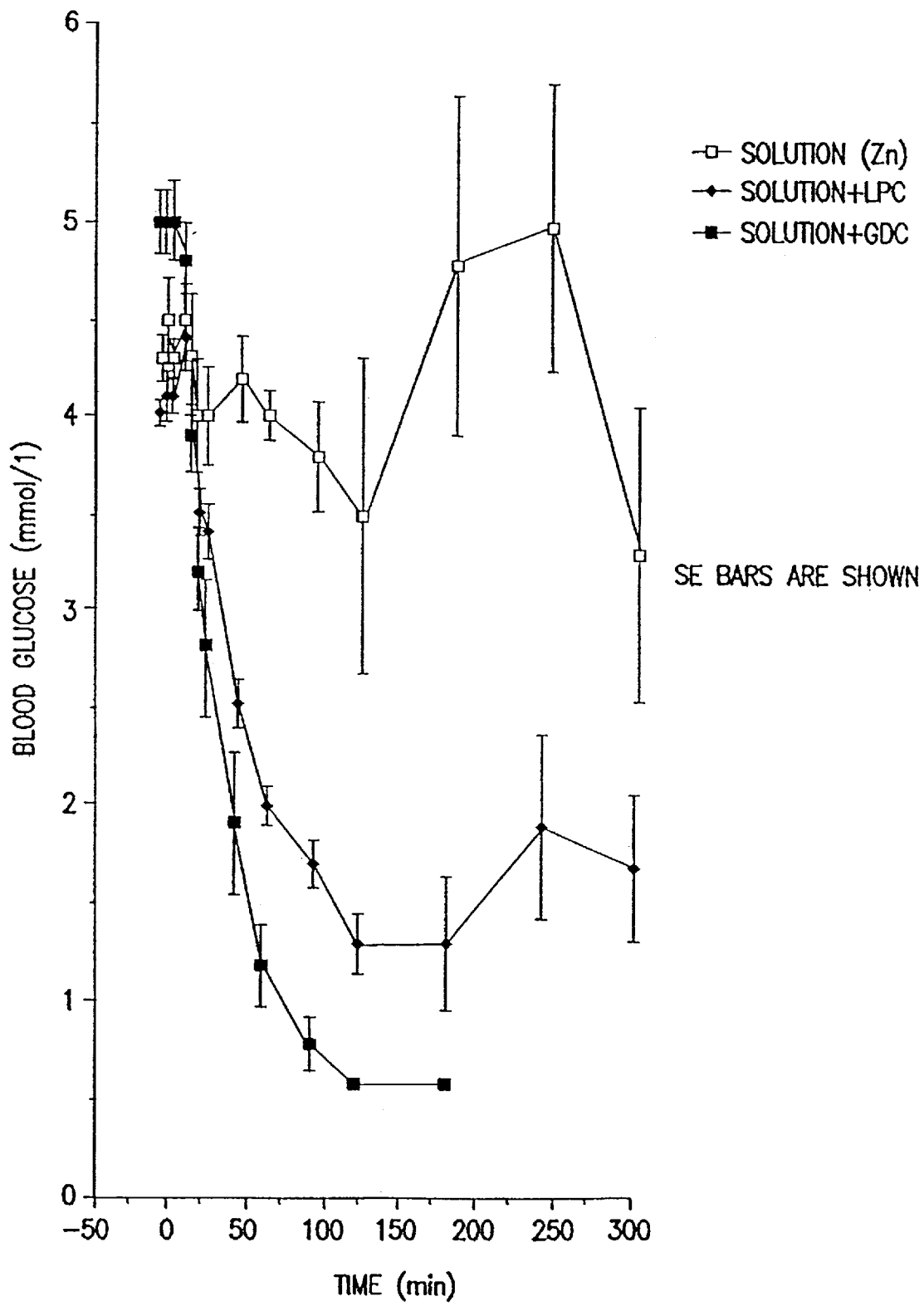

FIG. 3 shows the glucose levels for rats given intranasal doses of Zn-insulin solution, Zn-insulin solution in combination with 0.2% LPC or Zn-insulin solution in combination with 1% GDC. The results indicate that insulin given intranasally as a simple solution is not effective in lowering the plasma glucose level whereas the addition of a material such as LPC causes a fast and significant drop in measured plasma levels. The LPC in a concentration of 0.2% can be seen to have a similar effect to 1% bile salt in this in situ model where the cilia clearance mechanism is impaired.

Rabbit studies:

Preparations of Zn-insulin (mainly hexamer form) or Na-insulin (mainly monomer/dimer forms) were administered nasally to rabbits either as free insulin or as a microsphere delivery system with lysophosphatidylcholine (LPC) as a bioavailability increasing material. The experiments were performed in replicate (n=4).

Non-fasted New Zealand White female rabbits of average weight 3.5 kg were used in this study.

A 40 IU/ml Zn- or Na-human insulin solution was prepared in buffer (1/75M $Na_2HPO_4$) of pH 7.3–7.4. In some experiments 0.2% LPC was added.

A total of 200 μl of the solution (100 μl in each nostril) was administered intranasally equivalent to about 2.3 IU/kg using an Eppendorf pipette.

The rabbits were dosed s.c. with insulin at 0.8 IU/kg or 0.6 IU/kg from a 14 IU/ml or 10 IU/ml aqueous solution, respectively.

The dose of starch microspheres and insulin was fixed at 2.5 mg/kg and 2.5 IU/kg, respectively. The dose of LPC was 0.2 mg/kg. The average weight of the rabbits was 3.5 kg.

25 mg of microspheres were placed in a small glass vial and 250 μl of a 100 IU/ml insulin solution (Na- or Zn-insulin) was added followed by the 2 mg LPC and 250 μl of distilled water. The microspheres were then allowed to stand for 2 h at room temperature in contact with the insulin solution before freeze drying.

Approximately 15 mg of the freeze dried powder from each individual vial was filled into the applicator tubing, and this was stored in a dessicator until use.

The rabbits were administered the suggested dose into the nasal cavity without sedation. Each rabbit was held on its back during, and for 10 second after, the application to ensure the delivery of the powdered formulation. Blood samples of 200 μl and 2 ml for glucose and insulin determination, respectively, were collected from the marginal ear vein at 10 and 5 min prior to the administration and at 5, 15, 30, 45, 60, 90, 120 and 180 min post-administration. For insulin analysis, the blood collected was mixed gently in 5 ml heparinised (Li Heparin) tubes. For glucose analysis, the blood collected was mixed gently in 5 ml fluoride oxalate tubes. The blood samples for glucose analysis were kept on crushed ice awaiting immediate analysis. The blood samples for insulin analysis were spun at 3000 rpm and the plasma collected was stored at −20° C. awaiting analysis.

Figure 4:
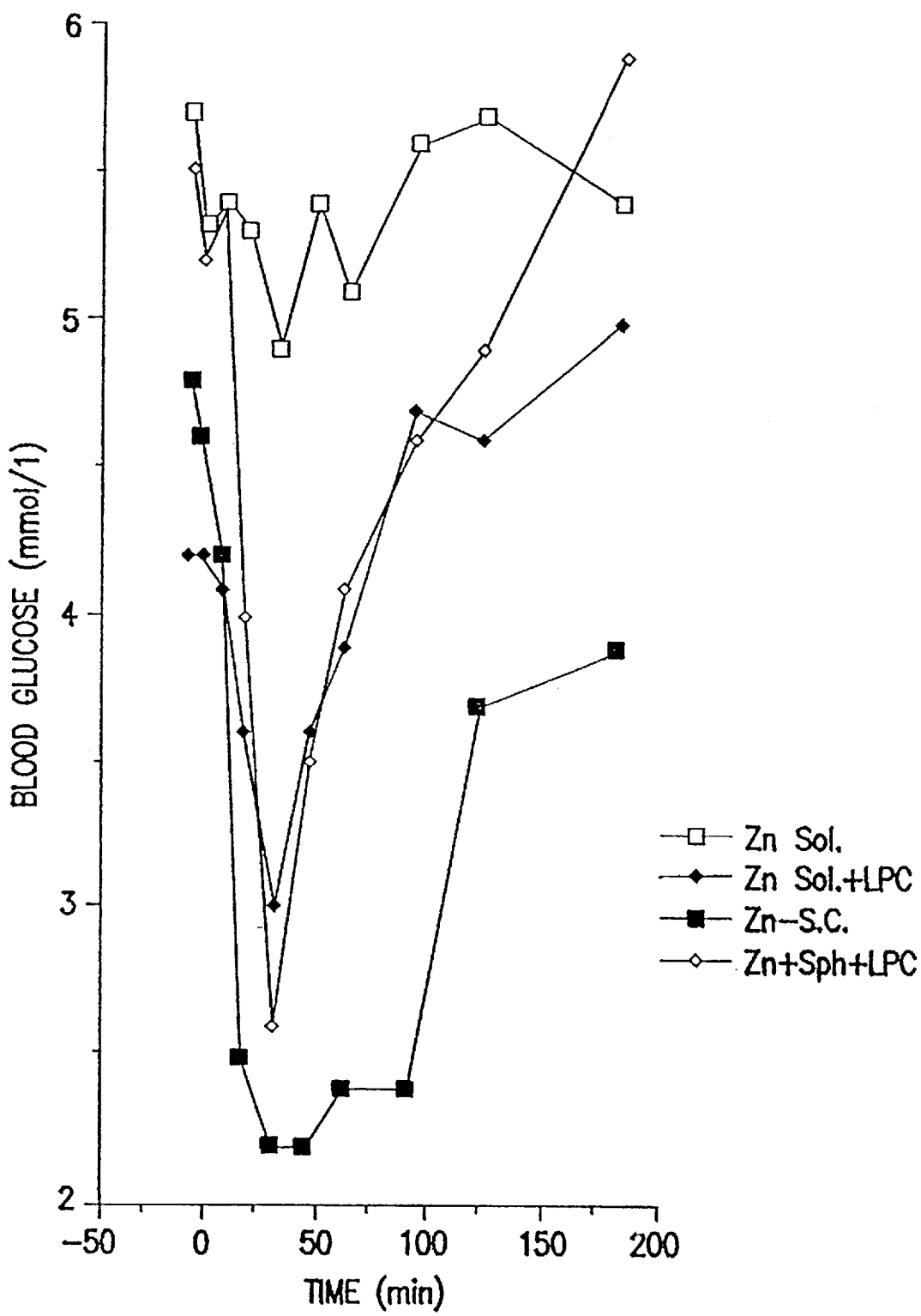
Figure 5:
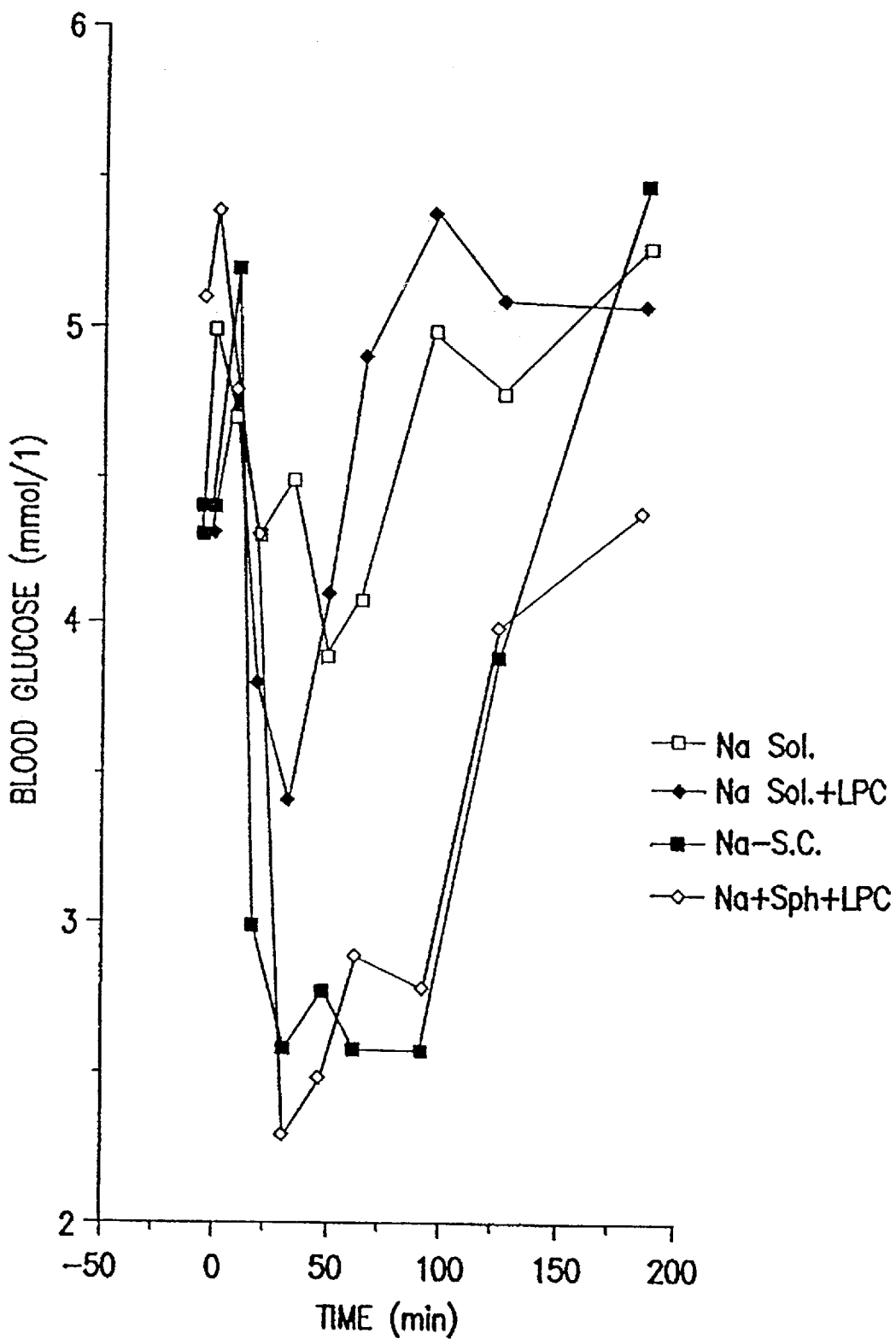

FIGS. 4 and 5 show the plasma glucose levels for rabbits given intranasal doses of Zn-insulin or Na-insulin, respectively as simple solutions, in simple solutions with 0.2% LPC added or in combination with starch microspheres and LPC. Also shown is the plasma glucose levels for rabbits injected s.c. with Zn-insulin or Na-insulin. The results show that for both types of insulin (hexameric and monomeric/dimeric form) the administration of the insulin in combination with the LPC the plasma glucose levels are lowered significantly compared to the simple insulin solutions. However, even more drastic decreases in plasma glucose levels are seen when the insulin is administered in combination with the microspheres and LPC. The shape of the plasma glucose curves for the latter systems are surprisingly similar to the ones obtained for the s.c. administration, although the doses are 2.5 IU/kg compared to 0.6 IU/kg for the s.c. dosing.

Sheep Studies

Zn-crystallized highly purified semisynthetic human insulin, each 1 mg of pure protein is equivalent to 28 IU insulin. Insulin solutions were prepared in 1/75M phosphate buffer (pH 7.3).

Fifteen cross-bred (Suffolk and Texel) sheep were used in this study. The animals were ear-tagged and weighed prior to the study:

The mean weight in kg of the sheep (±S.D.) was 35.9 (±2.7). The animals were not fasted prior to insulin administration because it is difficult to achieve this in practice and because of the possibility of inducing insulin resistance in the animals. The latter term means that under such conditions the sheep blood glucose levels would not respond as readily to the insulin administered.

An in-dwelling Viggo secalon universal central venous catheter of 1.2 mm i.d. with a secalon universal flow-switch was placed in the right jugular vein of each animal on the first day of the study and whenever necessary, was kept patent by flushing it with heparinised normal saline (50IU/ml). This catheter was removed upon the completion of the study.

Preparation of insulin solutions and powders:

Insulin stock solutions were prepared in 1/75M phosphate buffer (pH 7.3). These were then used as liquid formulations for intravenous and intranasal administration, and also in the preparation of the lyophilised microsphere formulations. The latter were prepared by dispersing the required quantity of micro-spheres in the insulin solution (+any LPC), stirring for 1 hour at room temperature, and then freeze-drying to obtain the powder formulation.

Administration of insulin formulations

Insulin was administered at 0.1 IU/kg via the intravenous route, at 0.2 IU/kg via the subcutaneous route, and at 2 IU/kg via the nasal route. Three sheep were used in each experiment:

(1) Intravenous administration of insulin as an aqueous solution prepared at 4 IU/ml : Sheep J, K, and L on 24/11/87.
(2) Intranasal administration of an aqueous solution, prepared at 200 IU/ml : Sheep A, B, and C on 24/11/87.
(3) Intranasal administration of an aqueous solution, prepared at 200 IU/ml in combination with 0.2% LPC (0.02 mg/kg) : Sheep D, E, and F on 24/11/87.
(4) Intranasal administration of insulin in combination with starch microspheres (2.5 mg/kg) and LPC (0.20 mg/kg) as a lyophilised powder. To prepare the formulation 500 mg of Spherex were dispersed in 30 ml of 1/75M phosphate buffer (pH 7.3) containing 400 IU insulin and 40 mg LPC, mixed for 1 h, and then freeze-dried : Sheep M, N and O on 26/11/87.
(5) Intranasal administration of starch microspheres (2.5 mg/kg) without insulin. To prepare the formulation, 500 mg of Spherex were dispersed in 30 ml of 1/75M phosphate buffer (pH 7.3) mixed for 1 h, and then freeze-dried: Sheep G, H, and I on 24/11/87.
(6) Subcutaneous administration of insulin as an aqueous solution prepared at 4.2 IU/ml.

For intranasal administration of solutions, a blueline umbilical cannula of 35 cm length (size 6FG, Portex Ltd., Hythe, Kent, England) was inserted into the nostril of the sheep to a preset depth of 10 cm before the delivery of the solution from a 1 ml syringe. For intranasal administration of powdered formulations, a BOC endotracheal tube (red rubber, cuffed) of 6.5 mm was loaded with the powder formulation and then inserted into the nostril of the sheep to a preset depth of 6 cm before blowing the powder into the nasal cavity.

For intranasal administration, the sheep were sedated by an i.v. dose of Ketamine hydrochloride at 2 mg/kg. This was intended as a counter-measure against the animal sneezing during administration. The anaesthesia lasts for about 3 minutes. The animals which received insulin by the i.v. route were also sedated to counter-act any possible effect of ketamine on the blood glucose or insulin levels measured.

Blood samples of 5 ml were collected onto crushed ice from the cannulated jugular vein of the sheep at 15 and 5 min prior to the insulin administration and at 5, 10, 15, 20, 30, 40, 50, 60, 75, 90, 120, 150, 180, and 240 min post-administration. Each blood sample was divided into two parts. For insulin analysis, the blood collected (2.5 ml) was mixed gently in 5 ml heparinised (Li Heparin) tubes. For glucose analysis, the blood collected (2.5 ml) was mixed gently in 5 ml fluoride oxalate tubes. All blood samples following withdrawal were maintained on crushed ice, awaiting centrifugation which was then performed at 4° C. and 3000 rpm. The plasma collected was stored at −20° C. awaiting insulin and glucose analysis (radioimmune assay for insulin).

Figure 6:
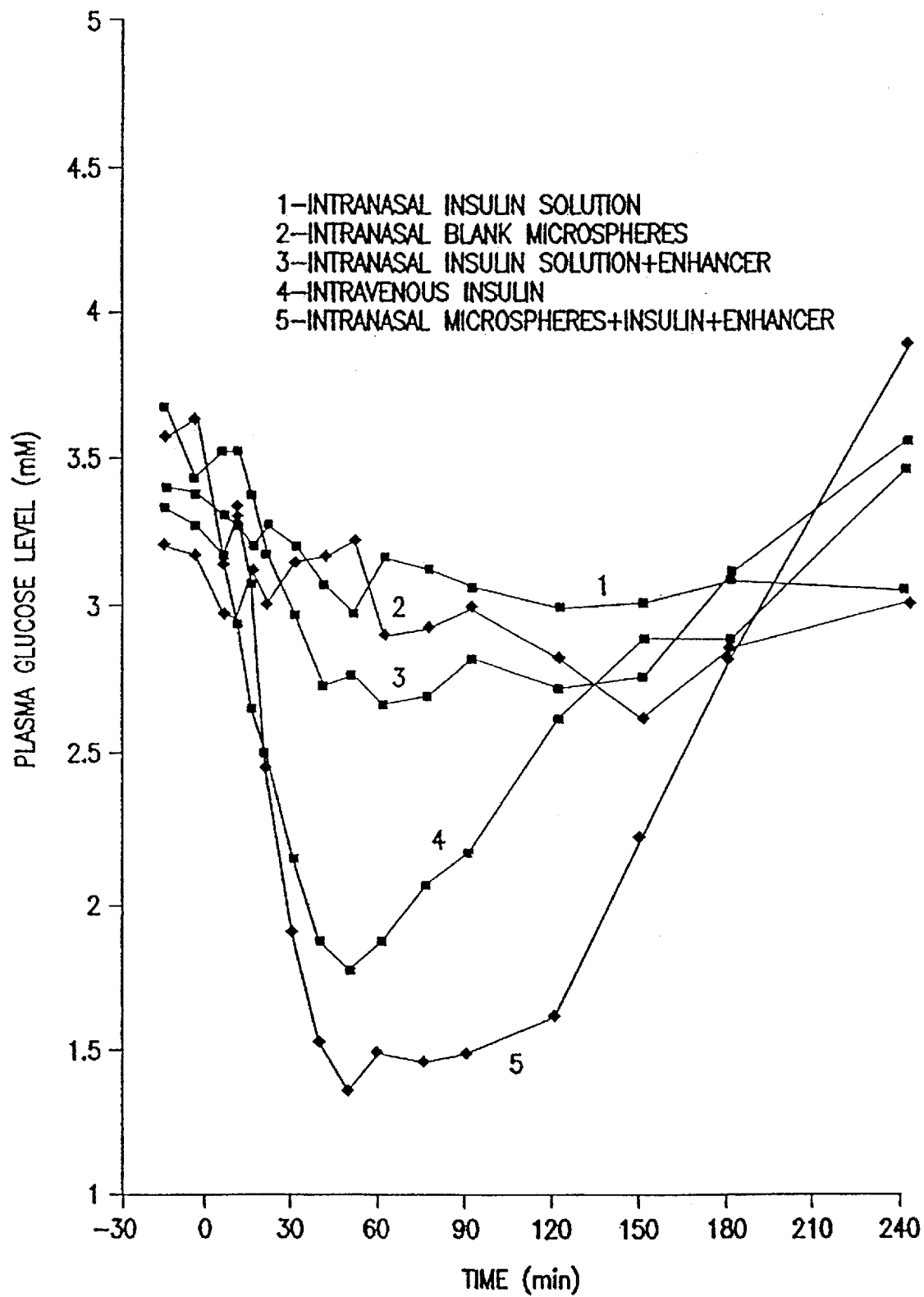
Figure 7:
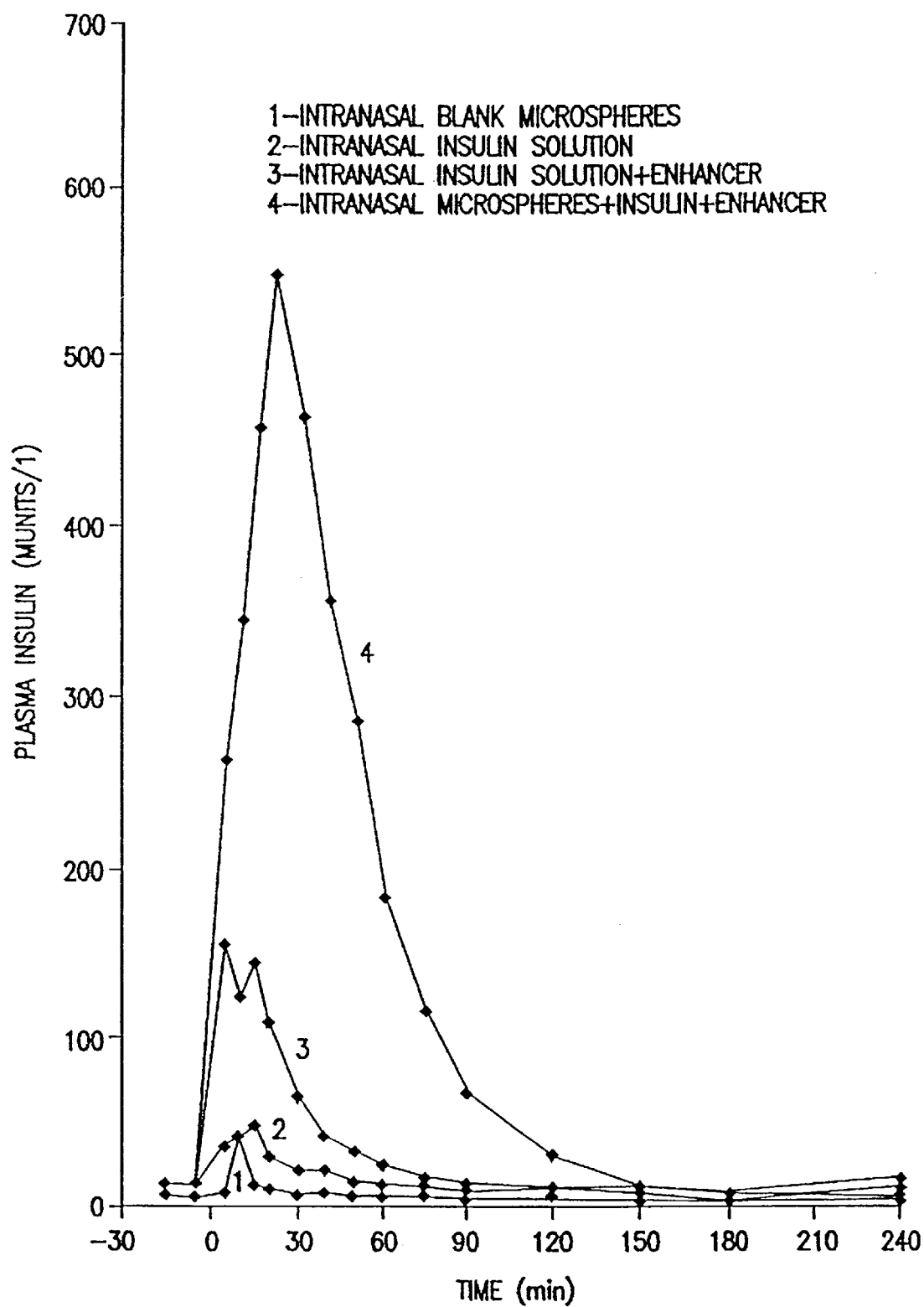

FIG. 6 shows the plasma glucose levels obtained for the administration intranasally of a simple insulin solution, of blank starch microspheres, of insulin solution with added 0.2% LPC, insulin as a microsphere formulation in combination with LPC and the intravenous administration of insulin. FIG. 7 shows the corresponding curves for plasma insulin levels. As seen in the rat and rabbit studies insulin administered intranasally as a simple solution does not have a significant effect on the plasma glucose level and the amount of insulin being absorbed via this route is indeed very low. Adding the (LPC) to the formulation increases the amount of insulin appearing in the circulation and hence results in a somewhat lower plasma glucose level. The administration of the insulin in combination the starch microspheres and LPC results in a 693% increase in AUC of plasma insulin as compared to a simple nasal insulin solution. At the same time the peak insulin level is increased with 1040%. The sharp level peak appears at 15–20 min and decreases rapidly as for intravenous insulin. Considering the glucose levels obtained when administering the insulin-microsphere-enhancer system the shape of the plasma glucose profile is very similar to the one obtained for the intravenous insulin. The relative bioavailability for this system is about 25% as compared to a subcutaneous injection of insulin.

The fact that the bioadhesive microsphere systems can provide plasma profiles similar to those obtained after IV dosing is very surprising. The bioadhesive microspheres seem to affect not only clearance but also absorption.

Human growth hormone

For all experiments biosynthetic hGH was used. The plasma levels were analysed using a solid-phase 2-site sandwich-ELISA technique. Plasma was assayed in duplicate at a dilution of 1/10 against a standard solution of B-hGH (0.11–7.0 ng/ml) prepared in antigen incubation buffer and also prepared in the appropriate dilution of plasma.

Rat studies:

As before the experiments were performed using the rat in situ model described by Hirai and modified by Fisher.

Non-fasted male Wistar rats of about 200 g were divided into groups of 4 and anaesthetized using an i.p. injection of 0.35 ml of pentobarbitone (60 mg/ml).

Three different hGH preparations were administered to the rats namely a 10 mg/ml solution of hGH in potassium phosphate buffer (1/75M), pH=7.2, as before with the addition of 0.05% LPC and as before with the addition of 0.5% LPC.

20 µl (1 mg/kg) of either of the three preparations were administered intranasally by means of a plastic tubing.

All experiments were performed in replicate. Blood samples, 20 drops were collected and kept on ice at times 0, 5, 10, 20, 30, 40, 50, 60, 90, 120, 180, 240 and 300 min after the application. The plasma was separated and stored at −20° C. until analysis.

Figure 8:
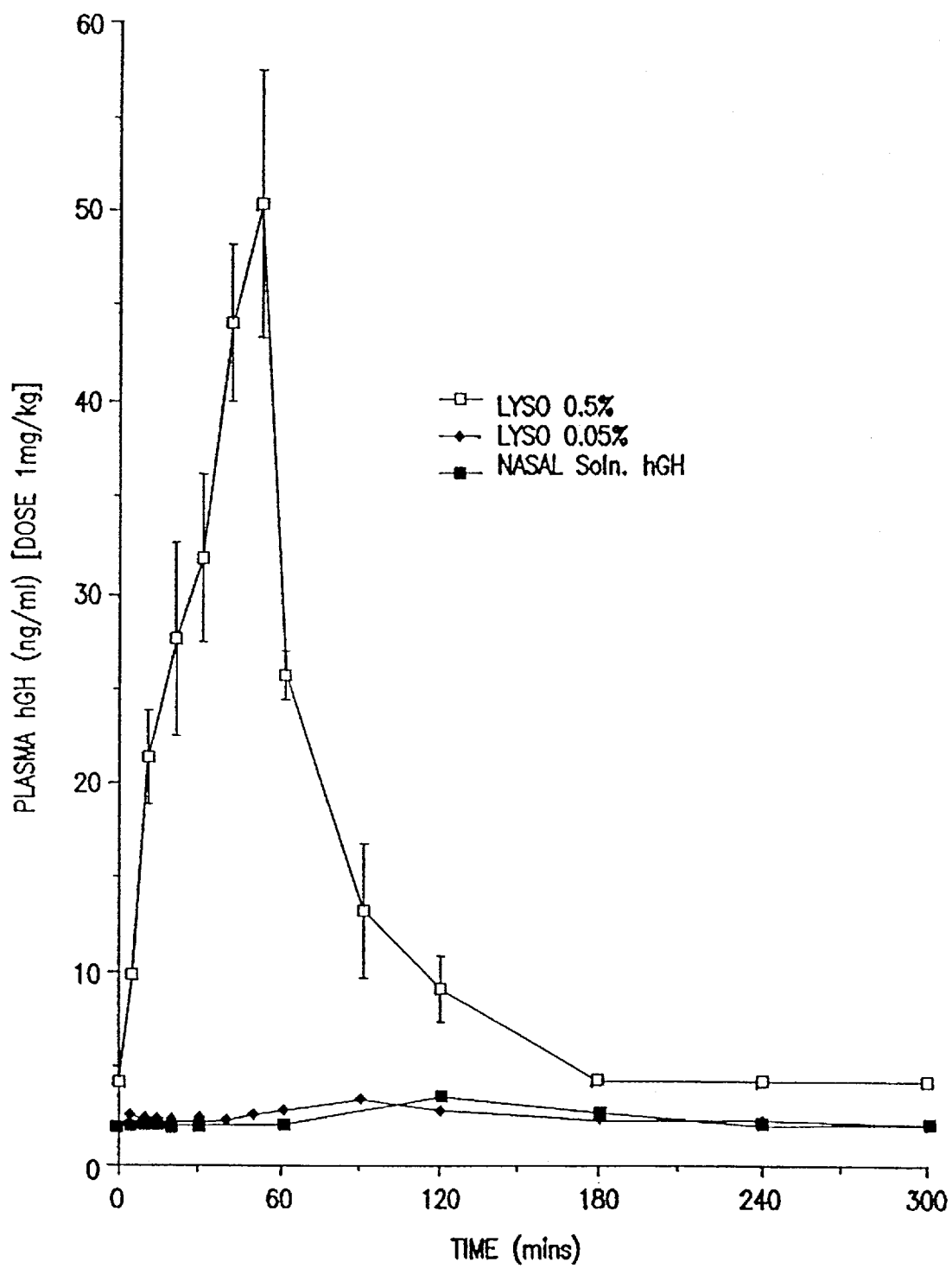

From FIG. 8 it can be seen that hGH given intranasally as a solution without an enhancer system is not absorbed at any significant degree via the nasal membrane. However with the addition of 0.5% LPC to the solution the resultant plasma level peaks are increased from about 3.5 ng/ml to about 57 ng/ml with a very significant increase in AUC. The addition of a very low concentration (0.05%) of LPC has apparently no effect on the absorption of hGH.

Sheep studies:

Twelve cross-bred (Suffolk and Texel) sheep were used in this study. The animals were ear-tagged and weighed prior to the study:

The mean weight in kg of the sheep (±S.D.) was 35.8 (±3.0).

An in-dwelling Viggo secalon universal central venous catheter of 1.2 mm i.d. with a secalon universal flow-switch was placed in the right jugular vein of each animal on the first day of the study and whenever necessary, was kept patent by flushing it with heparinised normal saline (25 IU/ml). This catheter was removed upon the completion of the study.

hGH was administered at 34.2 μg/kg (0.1 IU/kg) via the subcutaneous route and at 307.5 μg/kg (0.9 IU/kg) via the nasal route. Three sheep were used in each experiment:

(1) Subcutaneous administration of hGH as an aqueous solution prepared at 1.37 mg/ml (4 IU/ml).
(2) Intranasal administration of hGH as an aqueous solution prepared at 17.57 mg/ml (51.43 IU/ml). A sheep of 40 kg would thus receive 0.35 ml of the formulation in each nostril (0.70 ml total).
(3) Intranasal administration of hGH in combination with starch microspheres (2.5 mg/kg) and LPC (0.20 mg/kg) as a lyophilised powder. To prepare the formulation, 500 mg of Spherex were dispersed in 30 ml of sterile distilled water containing 61.5 mg hGH (180 IU) and 40 mg LPC, mixed for 1 h, and then freeze-dried:

For intranasal administration of solutions, a blue-line umbilical cannular of 35 cm length was inserted into the nostril of the sheep to a preset depth of 10 cm before the delivery of the solution from a 1 ml syringe. For intranasal administration of powdered formulation, a BOC endotracheal tube (red rubber, cuffed) of 6.5 mm was loaded with the powder formulation and then inserted into the nostril of the sheep to a preset depth of 6 cm before blowing the powder into the nasal cavity.

For the intranasal studies, it is necessary to sedate the sheep by use of an i.v. dose of Ketamine hydrochloride at 2 mg/kg. This is intended as a counter-measure against the animal sneezing during administration. The anaesthesia lasts for about 3 minutes.

The animals which received hGH by the s/c route were also sedated to counteract any possible effect of ketamine on the blood hGH levels measured.

Blood samples of 2 ml were collected in heparinised (Li Heparin) tubes onto crushed ice from the cannulated jugular vein of the sheep prior to the hGH administration and at 10, 20, 30, 40, 50, 60, 75, 90, 120, 150, 180, 240, and 300 min post-administration. The plasma collected by centrifugation (3000 rpm at 4° C.) were stored at −20° C. awaiting analysis by the ELISA technique.

Figure 9:
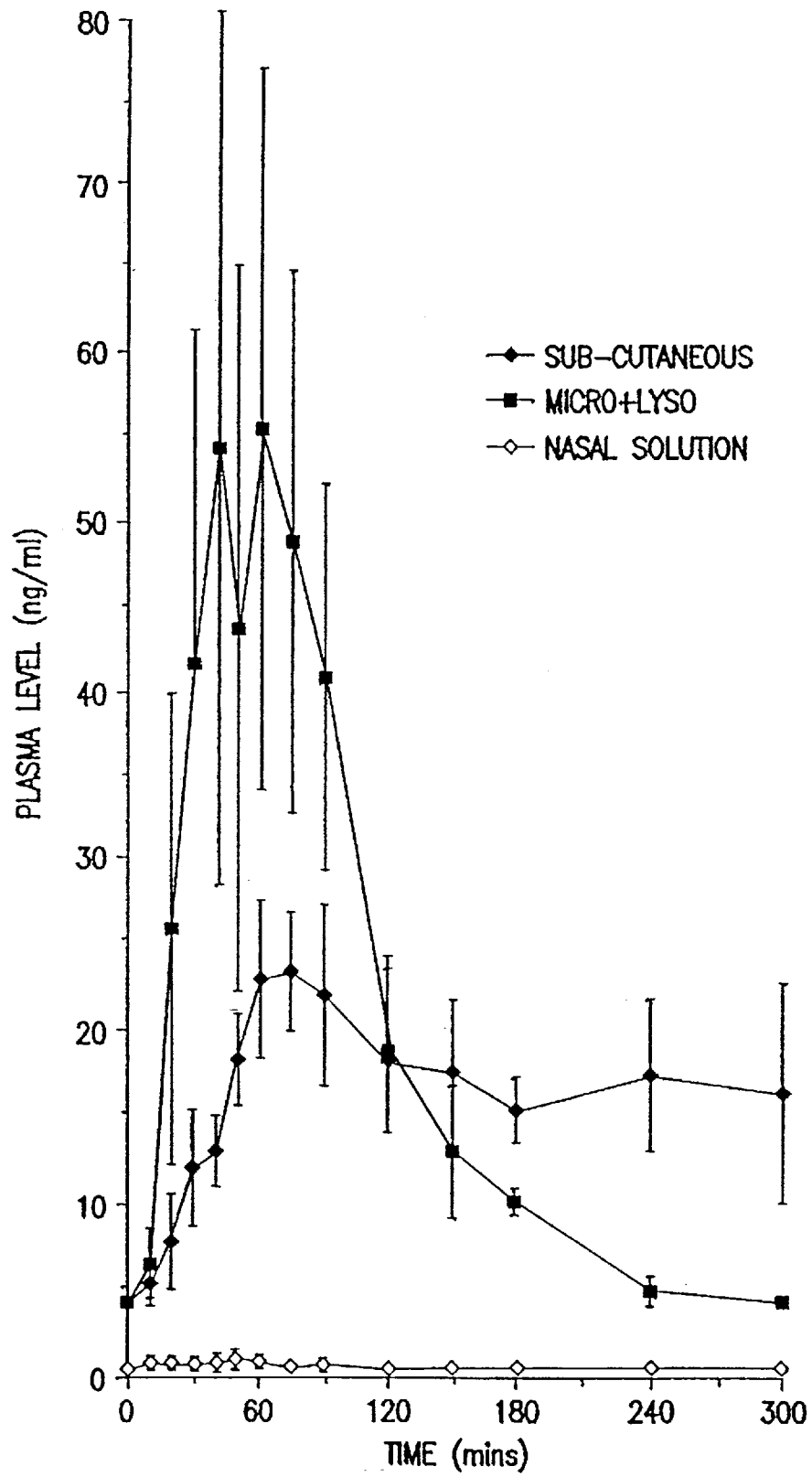

FIG. 9 shows the obtained hGH levels for the intranasal administration of a simple hGH solution, the intranasal administration of hGH in combination with microspheres and LPC and the subcutaneous injection of hGH. It can be concluded from the results that the hGH administered intranasally as a simple solution is not absorbed by any significant extent. However, when the hGH is administered in combination with microspheres and the LPC enhancer system the hGH plasma level is increased considerably. Thus, the peak plasma level is increased from about 10 ng/ml to about 55 ng/ml. The bioavailability as compared to subcutaneous injection can be calculated to about 20%.

The shape of the peak obtained using the microsphere-enhancer combination with LGH is also worthy of comment. A sharp peak, reminiscent of an intravenous dose is obtained. The subcutaneous administration of hGH gives a flatter profile, that reflects the slow release of the drug from the injection site. Thus as stated before for gentamycin and insulin the microspheres are not acting in a controlled release manner but providing a pronounced and surprising level of synergy when combined with the enhancing agent.

Comparative studies using insulin together with various materials

A series of studies were carried out to determine the effect on the administration of insulin of various enhancers with and without microsphere particles. All of the studies were carried out in sheep and the insulin was administered intranasally either in solution or powder formulation. The preparation of the various insulin formulations and the method of administration and result taking were all as described earlier.

Figure 10:
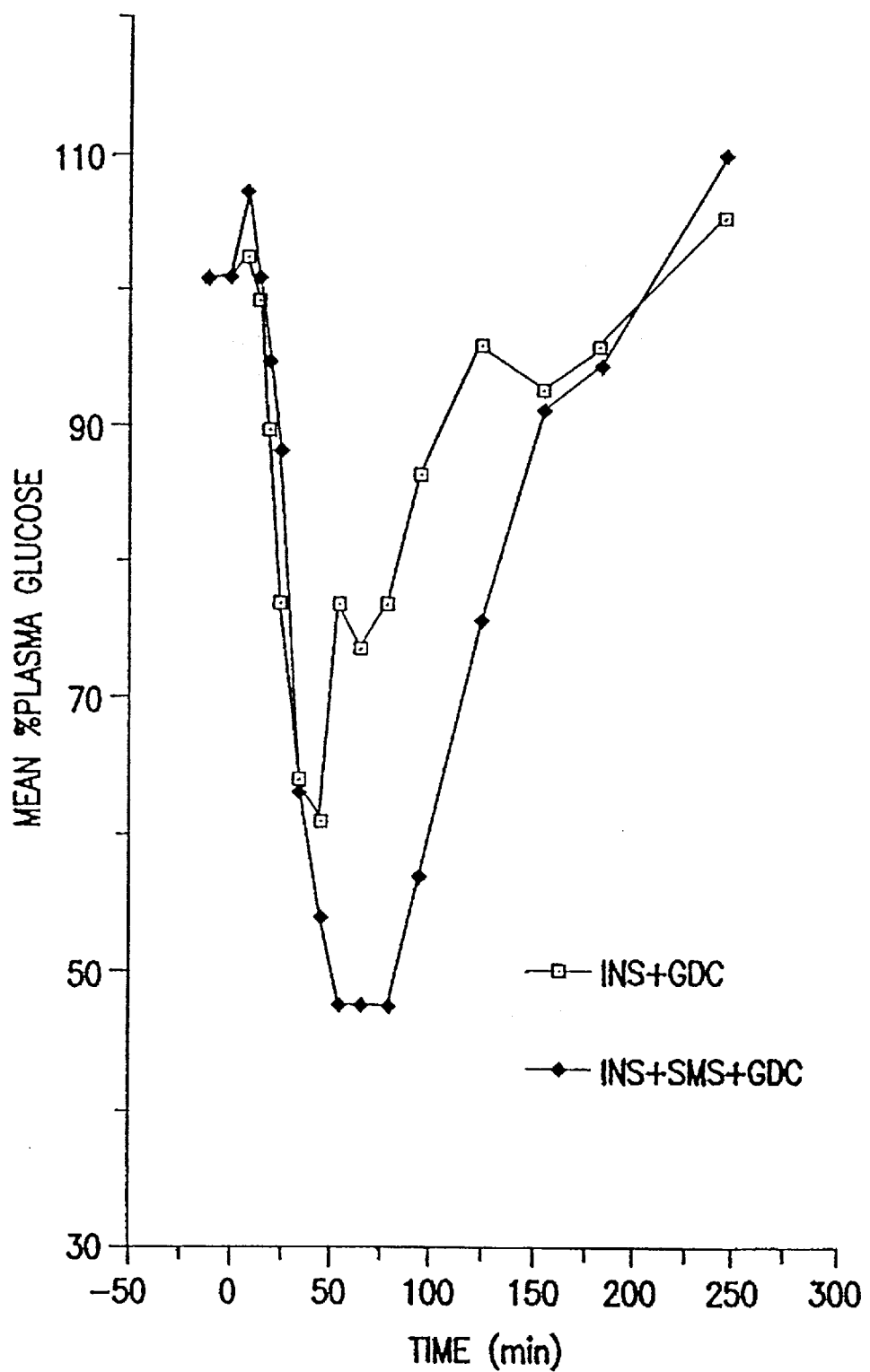
Figure 11:
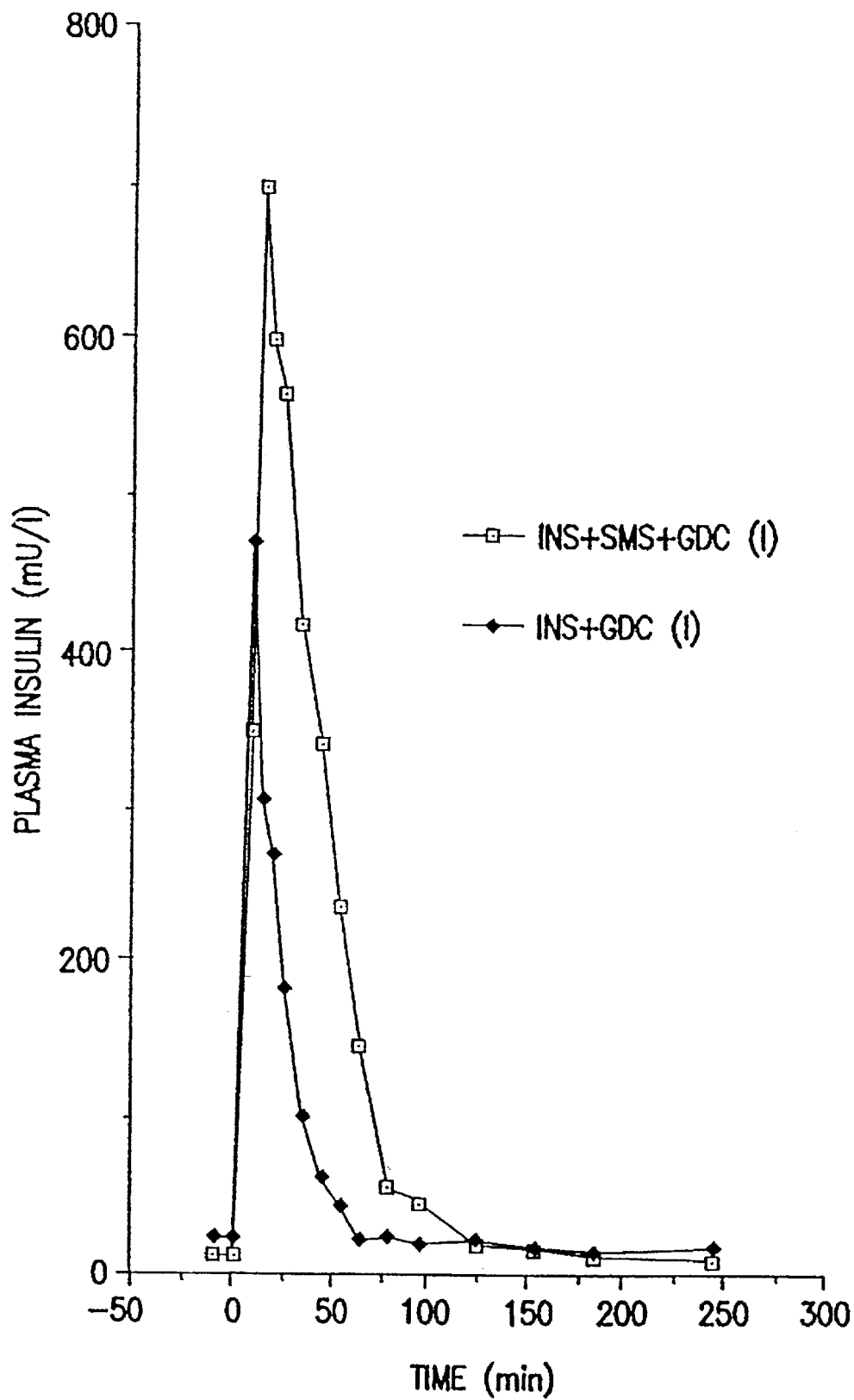

FIG. 10 shows the mean % plasma glucose levels following administration of insulin (INS). 2 IU/kg in combination with glycodeoxycholate (GDC) 0.08 mg/kg alone and with starch microspheres (SMS) 2.5 mg/kg and FIG. 11 shows the corresponding plasma insulin levels. It can be seen that the plasma glucose level is decreased considerably more by the administration of insulin with GDC and starch microspheres than by administration of insulin in the GDC solution. The corresponding plasma insulin levels demonstrate the enhanced absorption of insulin when administered with the microsphere formulation of the invention.

Figure 12:
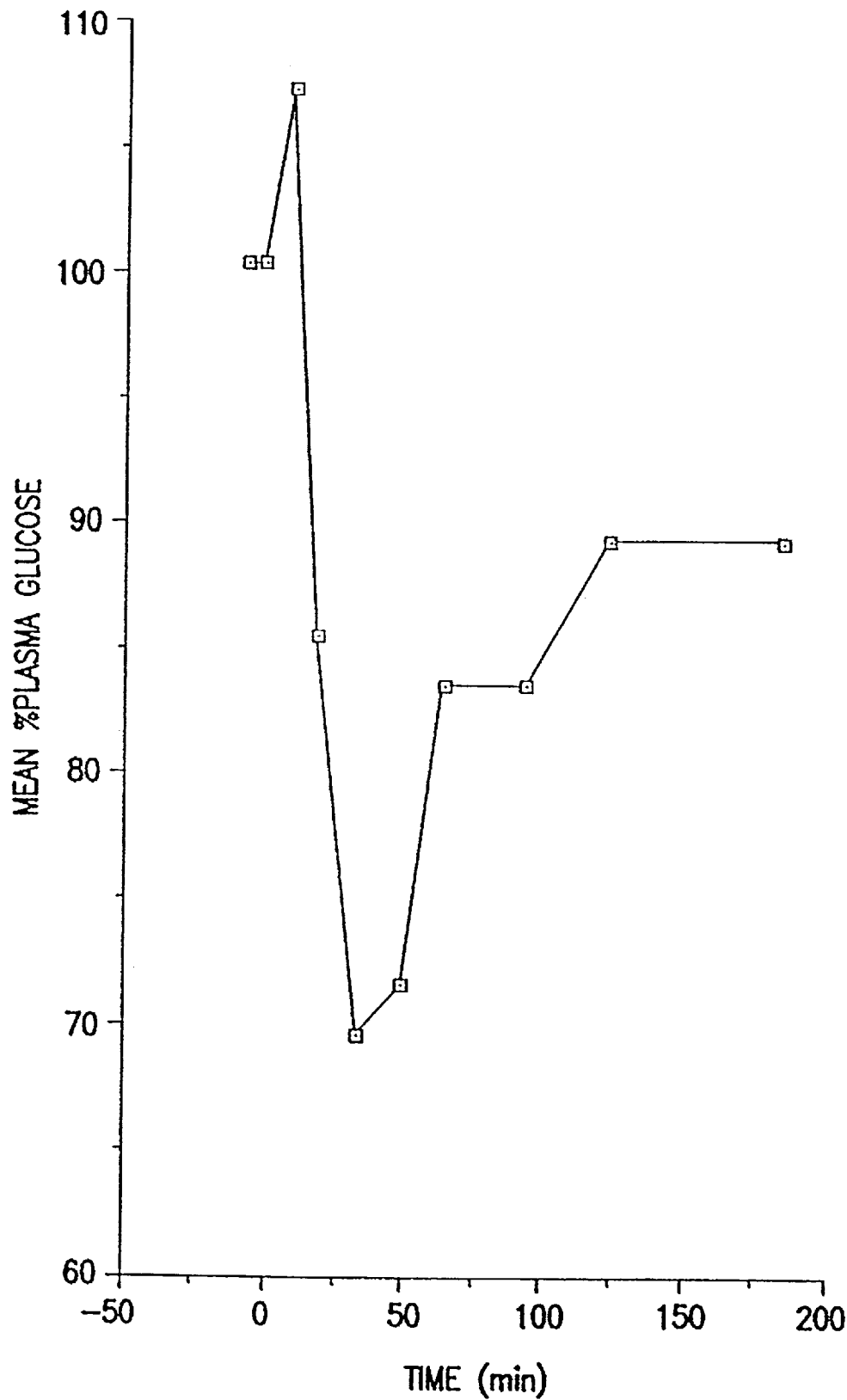

In FIG. 12, the results of administration of insulin together with starch microspheres and acyl-carmitine (CAR) are shown.

Figure 13:
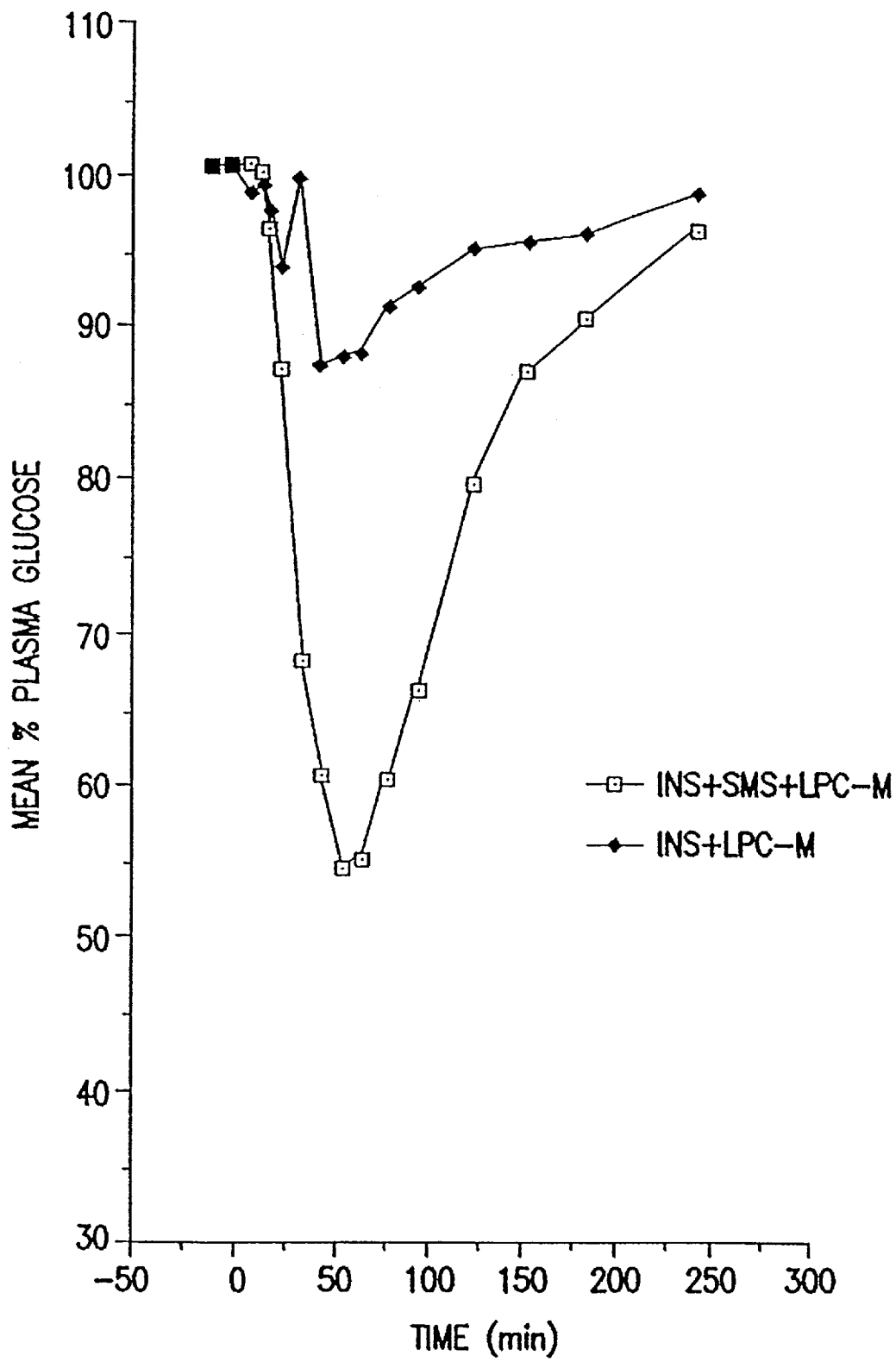
Figure 14:
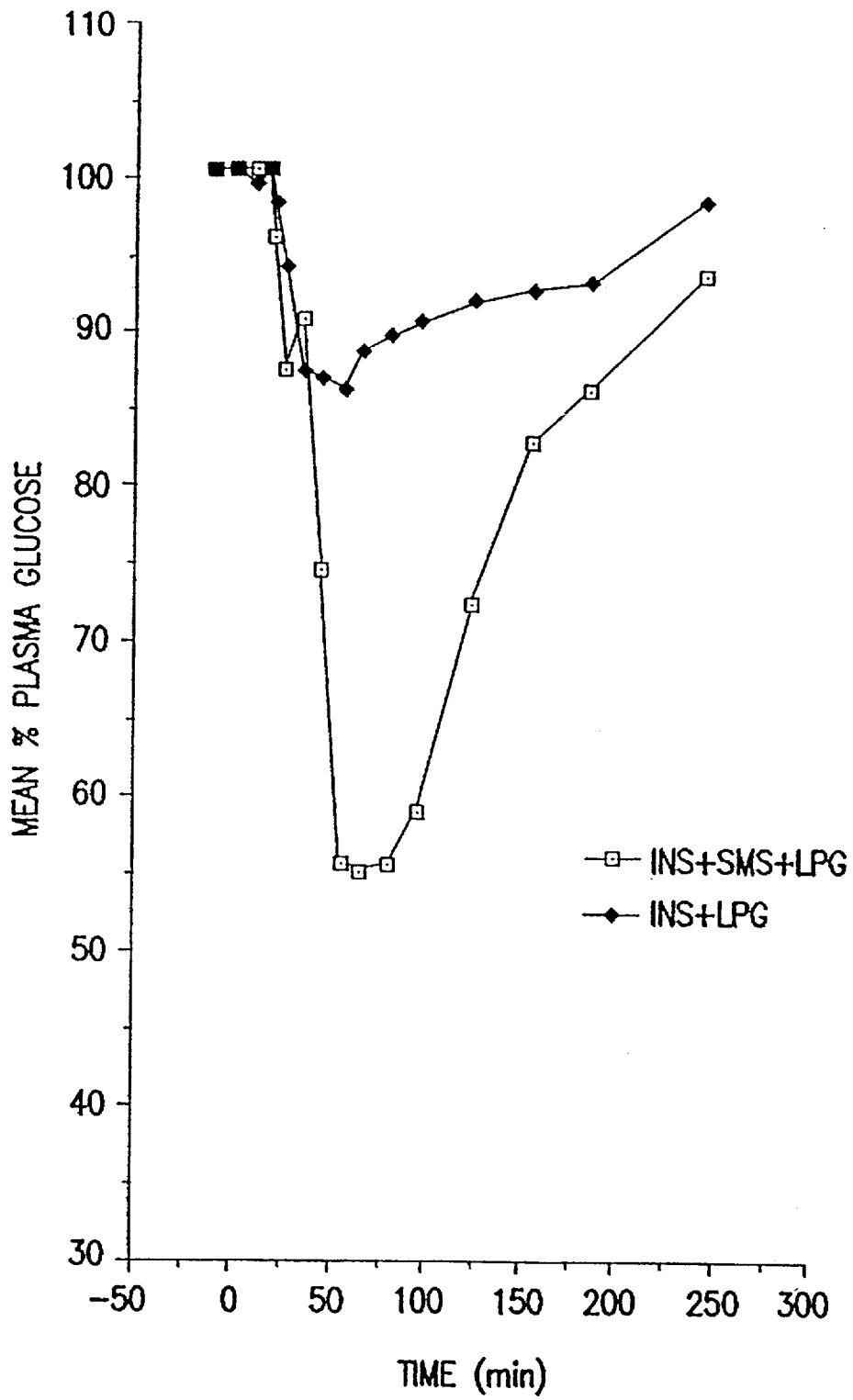
Figure 15:
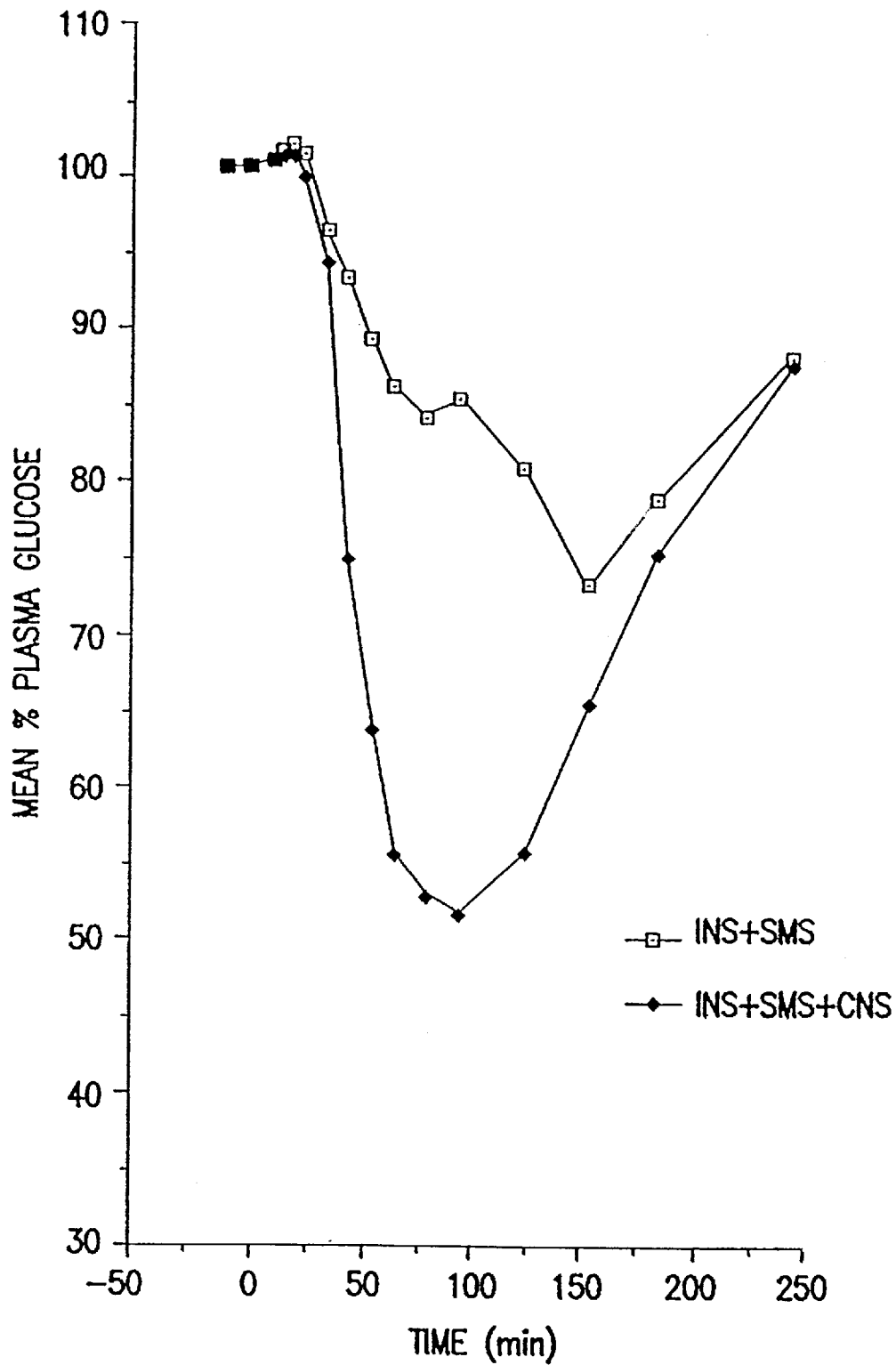

FIG. 13 demonstrates the considerably increased effect on plasma glucose levels found with administration of insulin in combination with lysophosphatidylcholine-myristoyl (LPC-M) and starch microspheres over administrations with LPC-M alone in solution. Similar results were found using lysophosphatidylglycerol (LPG) instead of LPC-M, (FIG. 14) and with chitosan (CNS) (FIG. 15).

FIGS. 16 and 17 shows the results of a study to compare changes in plasma glucose concentrations following administration of powder formulations of insulin with starch microspheres alone with those following administration of insulin with starch microspheres and a bioavailability increasing material. FIG. 16 shows the results using N-acetyl cysteine (N-Ac Cyst) and FIG. 17 shows the results using aprotinin. In both cases, the decrease in plasma glucose and hence the increase in absorption of insulin was considerably increased by the presence of the material.

In the above studies, it is interesting to note that the absorption profile of insulin shows a sharp peak, which is somewhat surprising. A flat sustained curve may have been expected as explained above.

All of the materials used in the above studies were found to be of comparative effectiveness.

References

1. Hussain, A., Hirai, S. and Bawarshi, R., Nasal absorption of natural contraceptive steroids in rats—progesterone absorption, J. Pharm. Sci. 70, 1981, 466–467.
2. Hussain, A., Hirai, S. and Bawarshi, R., Nasal absorption of propanolol from different dosage forms by rats and dogs, J. Pharm. Sci. 69, 1980. 1411–1413.

3. Salzman, R., Manson, J. E., Griffing, C. T., Kimmerle, R., Ruderman, N., McCall, A., Stoltz, E. I., Mullin, C., Small, D., Armstrong, J. and Melly, J. S., Intranasal aerosolized insulin, N. Eng. J. Med. 312, 1985,1078–1084.
4. Chien, Y. W., and Chang, S. F., Intranasal Dry Delivery for Systemic Medications CRC Critical Reviews in Therapeutic Drug Carrier Systems 4, 67 ug (1987).
5. Hanson, M., Gazdick, G., Cahill, J. and Augustine, M., Intranasal delivery of the peptide, salmon calcitonin, in S. S. Davis, L. Illum and E. Tomlinson: Advanced Delivery Systems for Peptides and Proteins, Plenum Press, London, 1986, pp. 233–242.
6. Gordon, G. F., Moses, A. C., Silver, R. D., Flier, G. F. and Carey, E., Nasal absorption of insulin: enhancement by hydrophobic bile salts, Proc. Natl. Acad. Sci. U.S.A. 82, 1985, 7419–7423.
7. Illum, L., Jorgenson, H., Bisgaard, H., Krogsgaard, O., and Rossing N., Bioadhesive microspheres as a potential nasal drug delivery system. Int. J. Pharmaceut. 39, 189–199 (1987).
8. Nagai, T., Nishimoto, Y., Nambu, N., Suzuki, Y. and Sekine, K., Powder dosage form of insulin for nasal administration, J. Control, Rel. 1, 1984, 15–22.
9. Morimoto, K., Morisaka, K. and Kamada, A., Enhancment of nasal absorption of insulin and calcitonin using polyacrylic acid gel, J. Pharm. Pharmacol. 37, 1985, 135–136.
10. S. S. Davis, L. Illum and E. Tomlinson (Eds). Delivery systems for peptide drugs, Plenum, New York, 1987.
11. de Vries, A. C. J., Batenburg, F. F. and van Golde, L. M. G. Lysophosphatidylcholine acyltransferase and lysophosphatidylcholine:lysophosphatidylcholine acyltransferase in alveolar type II cells from fetal rat lung. Biochem. Biophys. Acta 833 (1985) 93–99.
12. Christiansen, K. and Carlsen, J, Reconstitution of a protein into lipid vesicles using natural detergents. Biochim. Biophys. Acta 735 (1983) 225–233.
13. Davis S. S., Ilium, L. McVie, J. G. and Tomlinson E. (eds) Microspheres and Drug Therapy, Pharmaceutical, Immunological and Medical Aspects, Elsevier Science Publishers B. V., Amsterdam, 1983.
14. Fisher, A. N., Brown, K., Davis, S. S., Par, G. D. and Smith D. A., The effect of molecular size on the nasal absorption of water soluble compounds by the albino rat, J. Pharm. Pharmacol. 39, 1987, 357–362.
15. Hirai, S., Yashiki, T., Matsuzawa, T. and Mima, H., Absorption of drugs from the nasal mucosa of rat, Int. J. Pharm. 7, 1981, 317–325.
16. O'Connell, M. B., Hein, K., Halstenson, C. and Matzke, G. R. Heparin interference with tobramycin, netilmicin and gentamicin concentrations determined by EMIT. Drug Intell. Clin. Pharm. 18 (1984) 503–504.
17. Duchateau, G. S. M. J. E., Zuidema, F. and Merkus, W. H. M. Bile salts and intranasal drug absorption. Int. J. Pharm. 31 (1986) 193–199.

I claim:

1. A method for administering an active drug to a vertebrate, comprising administering to a mucosal membrane of the vertebrate bioadhesive microspheres of a size in the range of from about 10 micrometers to about 100 micrometers and formed of a material selected from the group consisting of proteins, polysaccharides, hyaluronic acid esters, and synthetic polymers, wherein each of the microspheres includes a physiologically effective amount of the active drug and an absorption enhancing material associated with each microsphere which enhances passage of the active drug through the membrane and increases the bioavailability of the active drug as compared to when the microspheres including the active drug are administered without the material, wherein the absorption enhancing material is selected from the group consisting of phospholipids, chelating agents, mucolytics, peptide inhibitors, and surface active agents selected from the group consisting of bile salts, fatty acids, fatty acid salts, acylglycerols, tyloxapols, acylcarnitine, fusidates, and mixtures thereof.

2. The method of claim 1 wherein the microspheres comprise a material selected from the group consisting of gelatin, albumin and collagen.

3. The method of claim 1 wherein the microspheres comprise a material selected from the group consisting of starch and dextran.

4. The method of claim 1 wherein the drug is a biologically active polypeptide.

5. The method of claim 1 wherein the absorption enhancing material is a biological surfactant selected from the group consisting of bile salts, fatty acids, fatty acid salts, acylglycerols, tyloxapols, acylcarnitines, phospholipids, lysophosphatides, fusidates, and mixtures thereof.

6. The method of claim 1 wherein the absorption enhancing material is selected from the group consisting of cyclodextrins, enamines, malonates, salicylates, glycyrrhetinates, chitosans, and mixtures thereof.

7. The method of claim 5 wherein the absorption enhancing material is a lysophosphatide.

8. The method of claim 7 wherein the absorption enhancing material is a lysophosphatidylcholine.

9. The method of claim 1 wherein the active agent and microspheres form a drug delivery system that is administered intranasally.

* * * * *